United States Patent [19]

Betschart et al.

[11] Patent Number: 5,780,501
[45] Date of Patent: Jul. 14, 1998

[54] TREATMENT METHOD USING ANTI-NEURODEGENERATIVELY ACTIVE 10-AMINOALIPHATYL-DIBENZ [B,F]OXEPINES

[75] Inventors: Claudia Betschart, Takarazuka, Japan; Kaspar Zimmermann, Riehen, Switzerland

[73] Assignee: Novartis Corporation, Summit, N.J.

[21] Appl. No.: 889,769

[22] Filed: Jul. 8, 1997

Related U.S. Application Data

[62] Division of Ser. No. 594,215, Jan. 31, 1996, abandoned.

[30] Foreign Application Priority Data

Feb. 8, 1995 [CH] Switzerland ................. 367/95

[51] Int. Cl.$^6$ ............................ A61K 31/335
[52] U.S. Cl. .......................... 514/450; 549/354
[58] Field of Search ................. 549/354; 514/450

[56] References Cited

U.S. PATENT DOCUMENTS

| 3,100,207 | 8/1963 | Zirkle et al. |
| 3,641,056 | 2/1972 | Schindler et al. |
| 3,928,383 | 12/1975 | Kaplan et al. |

FOREIGN PATENT DOCUMENTS

| 357126 | 3/1990 | European Pat. Off. |
| 436338 | 11/1967 | Switzerland |
| 440318 | 12/1967 | Switzerland |
| 1080979 | 8/1967 | United Kingdom |

OTHER PUBLICATIONS

Chemical Abstract, vol. 85, No. 11, Sep. 13, 1976, No. 77999v.

Chemical Abstract, vol. 81, No. 19, Nov. 11, 1974, No. 120510k.

Chemical Abstract, 85:78000z, (1976).

Primary Examiner—Robert W. Ramsuer
Attorney, Agent, or Firm—Marla J. Mathias; Gregory Ferraro

[57] ABSTRACT

Base-substituted dibenz[b,f]oxepines of formula I

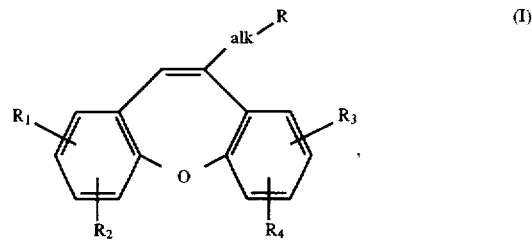

wherein alk is a divalent aliphatic radical, R is an amino group that is unsubstituted or mono- or di-substituted by monovalent aliphatic and/or araliphatic radicals or disubstituted by divalent aliphatic radicals, and $R_1$, $R_2$, $R_3$ and $R_4$ are each, independently of the others, hydrogen, lower alkyl, lower alkoxy, halogen or trifluoromethyl, and pharmaceutically acceptable salts thereof, may be used as anti-neurodegenerative active ingredients of medicaments. The invention relates also to novel compounds of formula I.

2 Claims, No Drawings

5,780,501

TREATMENT METHOD USING ANTI-NEURODEGENERATIVELY ACTIVE 10-AMINOALIPHATYL-DIBENZ [B,F]OXEPINES

This is a Divisional of Ser. No. 08/594,215, filed Jan. 31, 1996 now abandoned.

The invention relates to the use of 10-aminoaliphatyl-dibenz[b,f]oxepines of formula I

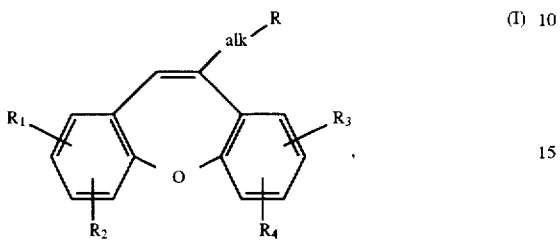

wherein alk is a divalent aliphatic radical,

R is an amino group that is unsubstituted or mono- or di-substituted by monovalent aliphatic and/or araliphatic radicals or disubstituted by divalent aliphatic radicals, and $R_1$, $R_2$, $R_3$ and $R_4$ are each, independently of the others, hydrogen, lower alkyl, lower alkoxy, halogen or trifluoromethyl, and pharmaceutically acceptable salts thereof, as anti-neurodegenerative active ingredients of medicaments and in the preparation thereof, and also to novel compounds of the formula I and salts thereof as such, to processes for the preparation thereof and to pharmaceutical compositions comprising them.

Novel compounds of formula I are, for example, 10-aminoaliphatyl-dibenz[b,f]oxepines in which a1) when in each case alk is methylene: R is other than methylamino, dimethylamino, N'-methylpiperazino and N'-(2-hydroxyethyl)piperazino or at least one of the radicals $R_1$, $R_2$ and $R_4$ is other than hydrogen or $R_3$ is other than hydrogen and 8-methoxy; R is other than dimethylamino and diethylamino or at least one of the radicals $R_1$, $R_2$ and $R_4$ is other than hydrogen or $R_3$ is other than 8-chloro; or: R is other than pyrrolidino or at least one of the radicals $R_1$, $R_2$, $R_3$ and $R_4$ is other than hydrogen, b1) when alk is ethylene: R is other than methylamino or at least one of the radicals $R_1$, $R_2$ and $R_4$ is other than hydrogen or $R_3$ is other than 6-methyl; or: R is other than diethylamino or at least one of the radicals $R_1$, $R_2$ and $R_4$ is other than hydrogen or $R_3$ is other than 7-methyl or at least one of the radicals $R_2$, $R_3$ and $R_4$ is other than hydrogen or $R_1$ is other than 3-methyl, c1) when alk is ethylidene: R is other than methylamino and dimethylamino or at least one of the radicals $R_1$, $R_2$ and $R_4$ is different from hydrogen, and d1) when alk is propylene: R is other than dimethylamino or at least one of the radicals $R_1$, $R_2$ and $R_4$ is other than hydrogen or $R_3$ is other than hydrogen or 8-trifluoromethyl; or at least one of the radicals $R_2$, $R_3$ and $R_4$ is other than hydrogen or $R_1$ is other than hydrogen or 3-trifluoromethyl or at least one of the radicals $R_2$ and $R_4$ is different from form hydrogen or $R_1$ is other than 3-chloro and $R_3$ is other than 8-chloro, or: R is other than piperidino, $R_2$, $R_3$ and $R_4$ are other than hydrogen or $R_1$ is other than 1-bromo or $R_1$, $R_2$ and $R_4$ are other than hydrogen or $R_3$ is other than 9-bromo;

preferably those in which a2) alk is different from methylene or ethylidene when R is amino, lower alkylamino or di-lower alkylamino or is an alkyleneamino, oxaalkyleneamino, azaalkyleneamino, N'-lower alkylazaalkyleneamino, N'-hydroxyalkylazaalkyleneamino or N'-alkanoyloxyalkylazaalkyleneamino radical having from 5 to 7 ring members that is bonded via nitrogen, $R_1$, $R_2$, $R_3$ and $R_4$ are hydrogen, lower alkyl, lower alkoxy, bromine or chlorine, and b2) alk is different from ethylene, 1,2- und 1,3-propylene, 1,2-, 1,3- und 1,4-butylene and 1,3-(2-methyl) propylene when R is a di-lower alkylamino, pyrrolidino, piperidino, N-lower alkylpiperidinyl, piperazino, N'-methylpiperazino, N'-formylpiperazino, N'-(2-hydroxyethyl)piperazino, N'-(2-acetoxyethyl) piperazino or N'-[2-(2-hydroxyethoxy)ethyl]piperazino radical, $R_1$ and $R_3$ are hydrogen, lower alkyl, lower alkoxy, halogen or trifluoromethyl and and $R_2$ and $R_4$ denote hydrogen, and c2) alk is different from methylene and ethylene when R is lower alkylamino, $R_1$ and $R_3$ are hydrogen, hydroxy, lower alkyl or lower alkoxy and $R_2$ and $R_4$ are hydrogen.

Monovalent aliphatic radicals are, for example, lower alkyl, lower alkenyl or lower alkynyl groups that are unsubstituted or substituted by free or etherified or esterified hydroxy or by unsubstituted or aliphatically substituted amino, such as lower alkyl, hydroxy-lower alkyl, lower alkoxy-lower alkyl, lower alkanoyloxy-lower alkyl, lower alkylamino-lower alkyl, di-lower alkylamino-lower alkyl, lower alkyleneamino-lower alkyl, lower alkenyl, hydroxy-lower alkenyl, lower alkoxy-lower alkenyl, lower alkanoyloxy-lower alkenyl, di-lower alkylamino-lower alkenyl, lower alkynyl, hydroxy-lower alkynyl, lower alkoxy-lower alkynyl, lower alkanoyloxy-lower alkynyl or di-lower alkylamino-lower alkynyl. Araliphatic radicals are, for example, phenyl-lower alkyl radicals that are unsubstituted or substituted by lower alkyl, lower alkoxy, halogen and/or by trifluoromethyl.

Amino groups that are mono- or di-substituted by monovalent aliphatic or araliphatic radicals are therefore, for example, lower alkylamino; phenyl-lower alkylamino or phenyl-lower alkyl-lower alkylamino each of which is unsubstituted or substituted by lower alkyl, lower alkoxy, halogen and/or by trifluoromethyl; hydroxy-lower alkylamino, lower alkoxy-lower alkylamino, lower alkanoyloxy-lower alkylamino, lower alkylamino-lower alkylamino, di-lower alkylamino-lower alkylamino, lower alkyleneamino-lower alkylamino, lower alkenylamino, hydroxy-lower alkenylamino, lower alkoxy-lower alkenylamino, lower alkanoyloxy-lower alkenylamino, di-lower alkylamino-lower alkenylamino, lower alkynylamino, hydroxy-lower alkynylamino, lower alkoxy-lower alkynylamino, lower alkanoyloxy-lower alkynylamino, di-lower alkylamino-lower alkynylamino, di-lower alkylamino, di(hydroxy-lower alkyl)amino, hydroxy-lower alkyl-lower alkylamino, di(lower alkoxy-lower alkyl)amino, lower alkoxy-lower alkyl-lower alkylamino, lower alkanoyloxy- lower alkylamino, lower alkanoyl oxy-lower alkyl-lower alkylamino, di-lower alkylamino-lower alkylamino, di-lower alkylamino-lower alkyl-lower alkylamino, di-lower alkenylamino, lower alkenyl-lower alkylamino, hydroxy-lower alkenyl-lower alkylamino, di(lower alkoxy-lower alkenyl)amino, lower alkoxy-lower alkenyl-lower alkylamino, lower alkanoyloxy-lower alkenyl-lower alkylamino, di-lower alkylamino-lower alkenyl-lower alkylamino, lower alkynyl-lower alkylamino, lower alkoxy-lower alkynyl-lower alkylamino, lower alkanoyloxy-lower alkynyl-lower alkylamino or di-lower alkylamino-lower alkynyl-lower alkylamino.

Divalent aliphatic radicals are, for example, lower alkylene radicals and, as a component of an amino group disubstituted by a divalent aliphatic radical, also aza-, oxa- or thia-lower alkylene radicals, such as 3- or 4-aza-lower alkylene that is unsubstituted or N-substituted by lower alkyl, hydroxy-lower alkyl, lower alkoxy-lower alkyl or by lower alkanoyl, 3- or 4-oxa-lower alkylene or optionally S-oxidised 3- or 4-thia-lower alkylene.

Amino groups disubstituted by divalent aliphatic radicals are, for example, 3- to 8-membered lower alkyleneamino, 3- or 4-aza-lower alkyleneamino that is unsubstituted or N-substituted by lower alkyl, hydroxy-lower alkyl, lower alkoxy-lower alkyl or by lower alkanoyl, 3- or 4-oxa-lower alkyleneamino or optionally S-oxidised 3- or 4-thia-lower alkyleneamino, such as, especially, pyrrolidino, piperidino, di-lower alkylpiperidino, hexamethyleneimino, heptamethyleneimino, piperazino, N'-lower alkylpiperazino, N'-hydroxy-lower alkyl-piperazino, N'-lower alkoxy-lower alkylpiperazino, N'-lower alkanoylpiperazino, morpholino, thiomorpholino, S-oxothiomorpholino or S,S-dioxothiomorpholino.

Hereinbefore and hereinafter there are to be understood by lower radicals and compounds, for example, those having up to and including 7, preferably up to and including 4, carbon atoms.

Di(hydroxy-lower alkyl)amino is, for example, N,N-di (hydroxy-$C_2$-$C_4$alkyl)amino, such as N,N-di(2-hydroxyethyl)amino or N,N-di(3-hydroxypropyl)amino.

Di(lower alkoxy-lower alkenyl)amino is, for example, N,N-di($C_1$-$C_4$alkoxy-$C_2$-$C_4$alkenyl)amino, such as N,N-di(4-methoxy-but-2-enyl)amino.

Di(lower alkoxy-lower alkyl)amino is, for example, N,N-di ($C_1$-$C_4$alkoxy-$C_1$-$C_4$alkyl)amino, such as N,N-di(2-methoxyethyl)amino, N,N-di(2-ethoxyethyl)amino or N,N-di(3-methoxypropyl)amino.

Di-lower alkenylamino is, for example, N,N-di-$C_2$-$C_4$alkenylamino, such as N,N-diallylamino or N-methallyl-N-allylamino.

Di-lower alkylamino is, for example, N,N-di-$C_1$-$C_4$alkylamino, such as dimethylamino, diethylamino, ethylmethylamino, dipropylamino, methylpropylamino, ethylpropylamino, dibutylamino or butylmethylamino.

Di-lower alkylamino-lower alkenyl-lower alkylamino is, for example, N-(di-$C_1$-$C_4$alkylamino-$C_2$-$C_4$alkenyl)-N-$C_1$-$C_4$alkylamino, such as N-(4-dimethylaminobut-2-enyl)-N-methylamino.

Di-lower alkylamino-lower alkenylamino is, for example, N-(di-$C_1$-$C_4$alkylamino-$C_2$-$C_4$-alkenyl)amino, such as N-(4-dimethylaminobut-2-enyl)amino.

Di-lower alkylamino-lower alkynylamino is, for example, N-(di-$C_1$-$C_4$alkylamino-$C_2$-$C_4$-alkynyl)amino, such as N-(4-dimethylaminobut-2-ynyl)amino.

Di-lower alkylamino-lower alkyl-lower alkylamino is, for example, N-(di-$C_1$-$C_4$alkylamino-$C_2$-$C_4$alkyl)-N-$C_1$-$C_4$alkylamino, such as N-(2-dimethylaminoethyl)-N-methylamino, N-(2-dimethylaminoethyl)-N-ethylamino, N-(3-dimethylaminopropyl)-N-methylamino or N-(4-dimethylaminobutyl)-N-methylamino.

Di-lower alkylamino-lower alkylamino is, for example, N-(di-$C_1$-$C_4$alkylamino-$C_2$-$C_4$alkyl)amino, such as N-(2-dimethylaminoethyl)amino, N-(2-dimethylaminoethyl)amino, N-(3-dimethylaminopropyl) amino or N-(4-dimethylaminobutyl)amino.

Halogen is, for example, halogen having an atomic number of up to and including 35, such as chlorine or bromine.

Hydroxy-lower alkenyl-lower alkylamino is, for example, N-(hydroxy-$C_2$-$C_4$alkenyl)-N-($C_1$-$C_4$alkylamino, such as N-(4-hydroxybut-2-enyl)-N-methylamino.

Hydroxy-lower alkenylamino is, for example, hydroxy-$C_2$-$C_4$alkenylamino, such as 4-hydroxybut-2-enylamino.

Hydroxy-lower alkynylamino is, for example, hydroxy-$C_2$-$C_4$alkynylamino, such as 4-hydroxybut-2-ynylamino.

Hydroxy-lower alkyl-lower alkylamino is, for example, N-(hydroxy-$C_2$-$C_4$alkyl)-N-$C_1$-$C_4$alkylamino, such as N-(2-hydroxyethyl)-N-methylamino, N-(3-hydroxypropyl)-N-methylamino or N-(4-hydroxybutyl)-N-methylamino.

Hydroxy-lower alkylamino is, for example, hydroxy-$C_2$-$C_4$alkylamino, such as 2-hydroxyethylamino, 3-hydroxypropylamino or 4-hydroxybutylamino.

N'-Hydroxy-lower alkylpiperazino is, for example, N'-(hydroxy-$C_1$-$C_4$alkyl)piperazino, such as N'-(2-hydroxyethyl)piperazino or N'-(3-hydroxypropyl) piperazino.

N'-Lower alkanoylpiperazino is, for example, N'-$C_1$-$C_7$alkanoylpiperazino, such as N'-acetylpiperazino.

N'-Lower alkoxy-lower alkylpiperazino is, for example, N'-($C_1$-$C_4$alkoxy-$C_1$-$C_4$alkyl)piperazino, such as N'-(2-methoxyethyl)piperazino or N'-(3-methoxypropyl) piperazino.

N'-Lower alkylpiperazino is, for example, N'-$C_1$-$C_4$alkylpiperazino, such as N'-methylpiperazino, N'-ethylpiperazino, N'-propylpiperazino or N'-butylpiperazino.

Lower alkoxy is, for example, $C_1$-$C_7$alkoxy, preferably $C_1$-$C_5$alkoxy, such as methoxy, ethoxy, propyloxy, isopropyloxy, butyloxy, isobutyloxy, sec-butyloxy, tert-butyloxy, pentyloxy or a hexyloxy or heptyloxy group.

Lower alkanoyloxy-lower alkenyl-lower alkylamino is, for example, N-($C_1$-$C_7$alkanoyloxy-$C_2$-$C_4$alkenyl)-N-($C_1$-$C_4$alkyl)amino, such as N-(4-acetoxybut-2-enyl)-N-methylamino.

Lower alkanoyloxy-lower alkenylamino is, for example, N-($C_1$-$C_7$alkanoyloxy-$C_2$-$C_4$-alkenyl)amino, such as N-(4-acetoxybut-2-enyl)amino.

Lower alkanoyloxy-lower alkynyl-lower alkylamino is, for example, N-($C_1$-$C_7$alkanoyloxy-$C_2$-$C_4$alkynyl)-N-($C_1$-$C_4$alkyl)amino, such as N-(4-acetoxybut-2-ynyl)-N-methylamino.

Lower alkanoyloxy-lower alkynylamino is, for example, N-($C_1$-$C_7$alkanoyloxy-$C_2$-$C_4$-alkynyl)amino, such as N-(4-acetoxybut-2-ynyl)amino.

Lower alkanoyloxy-lower alkyl-lower alkylamino is, for example, N-($C_1$-$C_7$alkanoyloxy-$C_2$-$C_4$-alkyl)-N-($C_1$-$C_4$alkyl)amino, such as N-(2-acetoxyethyl)-N-methylamino, N-(2-acetoxyethyl)-N-ethylamino, N-(3-acetoxypropyl)-N-methylamino or N-(4-acetoxybutyl)-N-methylamino.

Lower alkanoyloxy-lower alkylamino is, for example, N-($C_1$-$C_7$alkanoyloxy-$C_2$-$C_4$alkyl)amino, such as N-(2-acetoxyethyl)amino, N-(3-acetoxypropyl)amino or N-(4-acetoxybutyl)amino.

Lower alkenyl-lower alkylamino is, for example, N-($C_2$-$C_7$alkenyl)-N-($C_2$-$C_7$alkyl)amino, especially N-($C_2$-$C_4$alkenyl)-N-($C_1$-$C_4$alkyl)amino, such as N-vinyl-N-methylamino, N-allyl-N-methylamino, N-allyl-N-ethylamino, N-but-2-enyl-N-methylamino or N-but-3-enyl-N-methyl amino.

Lower alkenylamino is, for example, N-($C_2$-$C_7$alkenyl) amino, especially N-($C_2$-$C_4$-alkenyl)amino, such as vinylamino, allylamino, but-2-enylamino or N-but-3-enylamino, especially allylamino.

Lower alkynyl-lower alkylamino is, for example, N-($C_2$–$C_4$alkynyl)-N-($C_1$–$C_4$alkyl)amino, such as N-propargyl-N-methylamino, N-but-2-ynyl-N-methylamino or N-but-3-ynyl-N-methylamino.

Lower alkynylamino is, for example, N-($C_2$–$C_7$alkynyl)amino, especially N-($C_2$–$C_4$alkynyl)amino, such as propargylamino, but-2-ynylamino or N-but-3-ynylamino, especially propargylamino.

Lower alkoxy is, for example, $C_1$–$C_7$alkoxy, preferably $C_1$–$C_4$alkoxy, such as methoxy, ethoxy, propyloxy, isopropyloxy or butyloxy, but may also be isobutyloxy, sec-butyloxy, tert-butyloxy or a $C_5$–$C_7$alkoxy group, such as a pentyloxy, hexyloxy or heptyloxy group.

Lower alkoxy-lower alkenyl-lower alkylamino is, for example, N-($C_1$–$C_4$alkoxy-$C_2$–$C_4$alkenyl)-N-($C_1$–$C_4$alkyl)amino, such as N-(4-methoxybut-2-enyl)-N-methylamino, N-(4-methoxybut-2-enyl)-N-ethylamino or N-(4-ethoxybut-2-enyl)-N-methylamino.

Lower alkoxy-lower alkenylamino is, for example, N-($C_1$–$C_4$alkoxy-$C_2$–$C_4$alkenyl)amino, such as N-(4-methoxybut-2-enyl)amino or N-(4-ethoxybut-2-enyl)amino.

Lower alkoxy-lower alkynyl-lower alkylamino is, for example, N-($C_1$–$C_4$alkoxy-$C_2$–$C_4$alkynyl)-N-($C_1$–$C_4$alkyl)amino, such as N-(4-methoxybut-2-ynyl)-N-methylamino, N-(4-methoxybut-2-ynyl)-N-ethylamino or N-(4-ethoxybut-2-ynyl)-N-methylamino.

Lower alkoxy-lower alkynylamino is, for example, N-($C_1$–$C_4$alkoxy-$C_2$–$C_4$alkynyl)amino, such as N-(4-methoxybut-2-ynyl)amino, N-(4-ethoxybut-2-ynyl)amino or N-(4-propyloxybut-2-ynyl)amino.

Lower alkoxy-lower alkylamino is, for example, $C_1$–$C_4$alkoxy-$C_2$–$C_4$alkylamino, such as 2-methoxyethylamino, 2-ethoxyethylamino, 2-propyloxyethylamino, 3-methoxypropylamino, 3-ethoxypropylamino, 4-methoxybutylamino, 2-isopropyloxyethylamino or 2-butyloxyethylamino.

Lower alkoxy-lower alkyl-lower alkylamino is, for example, N-($C_1$–$C_4$alkoxy-$C_2$–$C_4$alkyl)-N-($C_1$–$C_4$alkyl)amino, such as N-(2-methoxyethyl)-N-methylamino, N-(2-ethoxyethyl)-N-methylamino, N-(2-propyloxyethyl)-N-methylamino, N-(3-methoxypropyl)-N-methylamino, 3-ethoxypropylamino or N-(4-methoxybutyl)-N-methylamino.

Lower alkyl is, for example, $C_1$–$C_7$alkyl, preferably $C_1$–$C_4$alkyl, such as methyl, ethyl, propyl, isopropyl or butyl, but may also be isobutyl, sec-butyl, tert-butyl or a $C_5$–$C_7$alkyl group, such as a pentyl, hexyl or heptyl group.

Lower alkylamino is, for example, $C_1$–$C_7$alkylamino, preferably $C_1$–$C_4$alkylamino, such as methylamino, ethylamino, propylamino, isopropylamino or butylamino, but may also be isobutylamino, sec-butylamino or tert-butylamino or a $C_5$–$C_7$alkylamino group, such as a pentylamino, hexylamino or heptylamino group, and is especially methylamino or propylamino.

Lower alkylamino-lower alkylamino is, for example, N-($C_1$–$C_4$alkylamino-$C_2$–$C_4$alkyl)amino, such as N-(2-methylaminoethyl)amino, N-(3-methylaminopropyl)amino, N-(4-methylaminobutyl)amino, N-(2-ethylaminoethyl)amino, N-(3-ethylaminopropyl)amino or N-(4-ethylaminobutyl)amino.

Lower alkyleneamino-lower alkylamino is, for example, 3- to 8-membered alkyleneamino-$C_2$–$C_4$alkylamino, such as 2-pyrrolidinoethylamino, 2-piperidinoethylamino, 2-dimethylpiperidinoethylamino, 2-hexamethyleneiminoethylamino, 3-pyrrolidinopropylamino, 3-piperidinopropylamino, 3-dimethylpiperidinopropylamino or 3-hexamethyleneiminopropylamino.

Phenyl-lower alkyl-lower alkylamino is, for example, N-(phenyl-$C_1$–$C_4$alkyl)-N-($C_1$–$C_4$alkyl)amino, such as N-benzyl-N-methylamino, N-(2-phenylethyl)-N-methylamino or N-(4-phenylbutyl)-N-methylamino.

Phenyl-lower alkylamino is, for example, phenyl-$C_1$–$C_4$alkylamino, such as benzylamino, 1- or 2-phenylethylamino, 3-phenylpropylamino or 4-phenylbutylamino.

Salts of compounds of formula I are, for example, the pharmaceutically acceptable acid addition salts thereof with suitable mineral acids, such as hydrohalic acids, sulfuric acid or phosphoric acid, for example hydrochlorides, hydrobromides, sulfates, hydrogen sulfates or phosphates, or salts with suitable aliphatic or aromatic sulfonic acids or N-substituted sulfamic acids, for example methanesulfonates, benzenesulfonates, p-toluenesulfonates or N-cyclohexylsulfamates (cyclamates).

Some of the compounds of formula I proposed for use in accordance with the invention are already known. For example there are proposed in German Offenlegungsschrift No. 1 793 521 as adrenolytic and central nervous system-dampening active ingredients of medicaments, such as sedative and narcosis-potentiating active ingredients of medicaments, compounds of formula I wherein alk is methylene or ethylidene and R is amino, methylamino, ethylamino, propylamino, isopropylamino, butylamino, isobutylamino, dimethylamino, diethylamino, dipropylamino, pyrrolidino, piperidino, morpholino, N'-methylpiperazino, N'-(2-hydroxyethyl)piperazino, N'-(2-acetoxyethyl)piperazino, N'-(2-pivaloyloxyethyl)piperazino or N'-methylhomopiperazino and $R_1$, $R_2$, $R_3$ and $R_4$ are hydrogen, lower alkyl, lower alkoxy and/or halogen.

The invention is based on the surprising discovery that compounds of formula I, at doses of approximately 0.1 mg/kg s.c. and below administered to newborn rats in an experimental or procedure according to Ausari et al., J. Neuroscience 13, 4042–4053 (1993), exhibit a pronounced protective action on facial motor neurons against apoptotic necrocytosis and, after the administration of 0.275 mg/kg s.c. and below to fully grown rats in an experimental procedure according to Golowitz and Paterson, Soc. Neurosc. Abstr. 20, 246, 113.2 (1994), exhibit a pronounced protective action on hippocampus pyramidal cells for a period of 4 days against necrocytosis caused by the administration of kainic acid.

The compounds of formula I and pharmaceutically acceptable salts thereof are accordingly, in addition to their previously known adrenolytic and central nervous system-dampening use, preferentially suited to the prophylactic or therapeutic treatment of neurodegenerative disorders, especially those in which apoptotic necrocytosis plays a part, such as cerebral ischaemias, Alzheimer's and Parkinson's disease, amyotrophic lateral sclerosis, glaucoma and also general or diabetic peripheral neuropathies.

The invention relates in the first line to the use of compounds of formula I wherein alk is lower alkylene, R is amino, lower alkylamino; phenyl-lower alkylamino or phenyl-lower alkyl-lower alkylamino each of which is unsubstituted or substituted by lower alkyl, lower alkoxy, halogen and/or by trifluoromethyl; hydroxy-lower alkylamino, lower alkoxy-lower alkylamino, lower alkanoyloxy-lower alkylamino, lower alkylamino-lower alkylamino, di-lower alkylamino-lower alkylamino, lower alkyleneamino-lower alkylamino, lower alkenylamino, hydroxy-lower alkenylamino, lower alkoxy-lower alkenylamino, lower alkanoyloxy-lower alkenylamino, di-lower alkylamino-lower alkenylamino, lower alkynylamino, hydroxy-lower alkynylamino, lower alkoxy-lower alkynylamino, lower alkanoyloxy-lower alkynylamino, di-lower alkylamino-lower alkynylamino, di-lower alkylamino, di(hydroxy-lower alkyl)amino, hydroxy-lower alkyl-lower alkylamino, di(lower alkoxy-lower alkyl)amino, lower alkoxy-lower alkyl-lower alkylamino, lower alkanoyloxy-lower alkylamino, lower alkanoyloxy-lower alkyl-lower alkylamino, di-lower alkylamino-lower alkylamino, di-lower alkylamino-lower alkyl-lower alkylamino, di-lower alkenylamino, lower alkenyl-lower alkylamino, hydroxy-lower alkenyl-lower alkylamino, di(lower alkoxy-lower alkenyl)amino, lower alkoxy-lower alkenyl-lower alkylamino, lower alkanoyloxy-lower alkenyl-lower alkylamino, di-lower alkylamino-lower alkenyl-lower alkylamino, lower alkynyl-lower alkylamino, lower alkoxy-lower alkynyl-lower alkylamino, lower alkanoyloxy-lower alkynyl-lower alkylamino, di-lower alkylamino-lower alkynyl-lower alkylamino, 3- to 8-membered lower alkyleneamino; 3- or 4-aza-lower alkyleneamino that is unsubstituted or N-substituted by lower alkyl, hydroxy-lower alkyl, lower alkoxy-lower alkyl or by lower alkanoyl; 3- or 4-oxa-lower alkyleneamino or optionally S-oxidised 3- or 4-thia-lower alkyleneamino and $R_1$, $R_2$, $R_3$ and $R_4$ are each, independently of the others, hydrogen, lower alkyl, lower alkoxy, halogen or trifluoromethyl, and pharmaceutically acceptable salts thereof, and also to novel compounds as defined above of formula I as such, especially those in which R is other than amino that is unsubstituted or mono- or di-substituted by lower alkyl, pyrrolidino, piperidino, morpholino, N'-methylpiperazino, N'-(2-hydroxyethyl)piperazino, N'-(2-acetoxyethyl)piperazino, N'-(2-pivaloyloxyethyl)piperazino and N'-methylhomopiperazino when alk is methylene or ethylidene and $R_1$, $R_2$, $R_3$ and $R_4$ are hydrogen, lower alkyl, lower alkoxy and/or halogen, and to salts thereof.

The invention relates especially to the use of compounds of formula I wherein alk is lower alkylene.

R is amino, lower alkylamino; phenyl-lower alkylamino or phenyl-lower alkyl-lower alkylamino each of which is unsubstituted or substituted by lower alkyl, lower alkoxy, halogen and/or by trifluoromethyl; lower alkenylamino, lower alkynylamino, di-lower alkylamino, 3- to 8-membered lower alkyleneamino; 3- or 4-aza-lower alkyleneamino that is unsubstituted or N-substituted by lower alkyl, hydroxy-lower alkyl, lower alkoxy-lower alkyl or by lower alkanoyl; 3- or 4-oxa-lower alkyleneamino or optionally S-oxidised 3- or 4-thia-lower alkyleneamino and $R_1$, $R_2$, $R_3$ and $R_4$ are each, independently of the others, hydrogen, lower alkyl, lower alkoxy, halogen or trifluoromethyl, and pharmaceutically acceptable salts thereof, and also novel compounds as defined above of formula I as such, especially those in which R is other than amino that is unsubstituted or mono- or di-substituted by lower alkyl, pyrrolidino, piperidino, morpholino, N'-methylpiperazino, N'-(2-hydroxyethyl)piperazino, N'-(2-acetoxyethyl)piperazino, N'-(2-pivaloyloxyethyl)piperazino and N'-methylhomopiperazino when alk is methylene or ethylidene and $R_1$, $R_2$, $R_3$ and $R_4$ are hydrogen, lower alkyl, lower alkoxy and/or halogen, and to salts thereof as well as to processes for the preparation thereof.

The invention relates especially to the use of compounds of formula I wherein alk is methylene.

R is amino, $C_1$-$C_4$alkylamino, such as methylamino, ethylamino, propylamino or butylamino; phenyl-$C_1$-$C_4$alkylamino, such as benzylamino or phenethylamino, that is unsubstituted or substituted by $C_1$-$C_4$alkyl, such as methyl, $C_1$-$C_4$alkoxy, such as methoxy, halogen having an atomic number of up to and including 35, such as chlorine or bromine, and/or by trifluoromethyl; phenyl-$C_1$-$C_4$alkyl-$C_1$-$C_4$alkylamino, such as N-benzyl-N-methylamino, that is unsubstituted or substituted by $C_1$-$C_4$alkyl, such as methyl, $C_1$-$C_4$alkoxy, such as methoxy, halogen having an atomic number of up to and including 35, such as chlorine or bromine, and/or by trifluoromethyl; $C_2$-$C_7$alkenylamino, such as allylamino, methallylamino or but-2-enylamino, $C_2$-$C_7$alkynylamino, such as propargylamino or but-2-ynylamino, N-$C_2$-$C_7$alkenyl-N-$C_1$-$C_4$alkylamino, such as N-allyl-N-methylamino, N-allyl-N-ethylamino, N-methallyl-N-methylamino or N-but-2-enyl-N-methylamino, N-$C_2$-$C_7$alkynyl-N-$C_1$-$C_4$alkylamino, such as N-propargyl-N-methylamino, N-propargyl-N-ethylamino or N-but-2-ynyl-N-methylamino, di-$C_1$-$C_4$alkylamino, such as dimethylamino, diethylamino, N-methyl-N-propylamino or N-butyl-N-methylamino, pyrrolidino, piperidino, morpholino, piperazino, N'-$C_1$-$C_4$alkylpiperazino, such as N'-methylpiperazino, or N'-(hydroxy-$C_2$-$C_4$alkyl)piperazino, such as N'-(2-hydroxyethyl)piperazino, and $R_1$, $R_2$, $R_3$ and $R_4$ are each, independently of the others, hydrogen, $C_1$-$C_4$alkyl, such as methyl, $C_1$-$C_4$alkoxy, such as methoxy, halogen having an atomic number of up to and including 35, such as chlorine or bromine, or trifluoromethyl, and pharmaceutically acceptable salts thereof, and also to novel compounds as defined above of formula I as such, especially those in which R is other than amino, $C_1$-$C_4$alkylamino, di-$C_1$-$C_4$alkylamino, pyrrolidino, piperidino, morpholino and N'-methylpiperazino when $R_1$, $R_2$, $R_3$ and $R_4$ are hydrogen, $C_1$-$C_4$alkyl, $C_1$-$C_4$alkoxy and/or halogen, and to salts thereof as well as to processes for the preparation thereof.

The invention relates more especially to compounds of formula I wherein alk is methylene, R is $C_2$-$C_7$alkenylamino, such as allylamino, methallylamino or but-2-enylamino, $C_2$-$C_7$alkynylamino, such as propargylamino or but-2-ynylamino, N-$C_2$-$C_7$alkenyl-N-$C_1$-$C_4$alkylamino, such as N-allyl-N-methylamino, N-allyl-N-ethylamino, N-methallyl-N-methylamino or N-but-2-enyl-N-methylamino, N-$C_2$-$C_7$alkynyl-N-$C_1$-$C_4$alkylamino, such as N-propargyl-N-methylamino, N-propargyl-N-ethylamino or N-but-2-ynyl-N-methylamino, or pyrrolidino, piperidino or morpholino, $R_1$ and $R_3$ are each, independently of the others, hydrogen, $C_1$-$C_4$alkyl, such as methyl, $C_1$-$C_4$alkoxy, such as methoxy, halogen having an atomic number of up to and including 35, such as chlorine or bromine, or trifluoromethyl, and $R_2$ and $R_4$ are hydrogen, and to salts thereof, and to processes for the preparation thereof as well as to the use thereof.

The invention relates most especially to compounds of formula I wherein alk is methylene, R is $C_2$-$C_7$alkenylamino, such as allylamino, methallylamino or but-2-enylamino, $C_2$-$C_7$alkynylamino, such as propargylamino or but-2-ynylamino, N-$C_2$-$C_7$alkenyl-N-$C_1$-$C_4$alkylamino, such as N-allyl-N-methylamino, N-allyl-N-ethylamino, N-methallyl-N-methylamino or N-but-2-enyl-N-methylamino, N-$C_2$-$C_7$alkynyl-N-$C_1$-$C_4$alkylamino, such as N-propargyl-N-methylamino, N-propargyl-N-ethylamino or N-but-2-ynyl-N-methylamino, or phenyl-$C_1$-$C_4$alkylamino, such as benzylamino or phenethylamino, that is unsubstituted or substituted by $C_1$-$C_4$alkyl, such as methyl, $C_1$-$C_4$alkoxy, such as methoxy, halogen having an atomic number of up to and including 35, such as chlorine or bromine, and/or by trifluoromethyl, and $R_1$, $R_2$, $R_3$ and $R_4$ are hydrogen, and to salts thereof, and to processes for the preparation thereof as well as to the use thereof.

The invention relates specifically to the use of

N-(dibenz|b,f|oxepin-10-ylmethyl)-N-methyl-N-prop-2-ynylamine;
N-allyl-N-(dibenz|b,f|oxepin-10-ylmethyl)amine;
N-allyl-N-(dibenz|b,f|oxepin-10-ylmethyl)-N-methylamine;
N-(dibenz|b,f|oxepin-10-ylmethyl)amine;
N-(dibenz|b,f|oxepin-10-ylmethyl)-N-prop-2-ynylamine;
N-(dibenz|b,f|oxepin-10-ylmethyl)-N-propylamine;
N-(dibenz|b,f|oxepin-10-ylmethyl)-N-methyl-N-propylamine;
1-dibenz[b,f]oxepin-10-ylmethyl-piperidine;
4-dibenz[b,f]oxepin-10-ylmethyl-morpholine;
N-(1-chloro-dibenz|b,f|oxepin-10-ylmethyl)-N-methyl-N-prop-2-ynylamine;
1-(1-chloro-dibenz|b,f|oxepin-10-ylmethyl)-pyrrolidine;
N-(1-chloro-dibenz|b,f|oxepin-10-ylmethyl)-N-methyl-N-propylamine;
N-methyl-N-prop-2-ynyl-N-(3-trifluoromethyl-dibenz[b,f|oxepin-10-ylmethyl)amine
1-(3-trifluoromethyl-dibenz[b,f]oxepin-10-ylmethyl)-pyrrolidine;
N-(7-chloro-dibenz[b,f|oxepin-10-ylmethyl)-N-methyl-N-prop-2-ynylamine;
1-(7-chloro-dibenz[b,f|oxepin-10-ylmethyl)-pyrrolidine;
N-(8-methoxy-dibenz[b,f|oxepin-10-ylmethyl)-N-methyl-N-prop-2-ynylamine;
N-(8-tert-butyl-dibenz[b,f|oxepin-10-ylmethyl)-N-methyl-N-prop-2-ynylamine;
1-(8-tert-butyl-dibenz[b,f|oxepin-10-ylmethyl)-pyrrolidine;
N-(6-chloro-dibenz[b,f|oxepin-10-ylmethyl)-N-methyl-N-prop-2-ynylamine;
1-(6-chloro-dibenz[b,f|oxepin-10-ylmethyl)pyrrolidine;
N-(1-fluoro-dibenz|b,f|oxepin-10-ylmethyl)-N-methyl-N-prop-2-ynylamine;
1-(1-fluoro-dibenz[b,f|oxepin-10-ylmethyl)pyrrolidine;
N-(dibenz[b,f|oxepin-10-ylmethyl)-N-benzylamine;
N-benzyl-N-(dibenz|b,f|oxepin-10-ylmethyl)-N-methylamine;
N-(dibenz|b,f|oxepin-10-ylmethyl)-N-propyl-N-benzylamine;
N-allyl-N-benzyl-N-(dibenz|b,f|oxepin-10-ylmethyl)amine;
1-(dibenz[b,f|oxepin-10-ylmethyl)-4-methyl-piperazine;
1-(dibenz|b,f|oxepin-10-ylmethyl)-4-(2-hydroxyethyl)-piperazine;
N,N-diethyl-N-(dibenz|b,f|oxepin-10-ylmethyl)amine;
N-(dibenz|b,f|oxepin-10-ylmethyl)-N,N-dimethylamine;
N-(dibenz|b,f|oxepin-10-ylmethyl)-N-methylamine;
1-(dibenz|b,f|oxepin-10-ylmethyl)pyrrolidine;
N-|1-(dibenz|b,f|oxepin-10-ylethyl)-N,N-dimethylamine;
N-|1-(dibenz|b,f|oxepin-10-ylethyl)-N-methylamine;
1-(8-methoxy-dibenz|b,f|oxepin-10-ylmethyl)-4-methyl-piperazine;
N-(8-methoxy-dibenz|b,f|oxepin-10-ylmethyl)-N,N-dimethylamine;
N-(8-methoxy-dibenz|b,f|oxepin-10-ylmethyl)-N-methylamine;
N-(dibenz|b,f|oxepin-10-ylmethyl)amine;
N-butyl-N-(dibenz|b,f|oxepin-10-ylmethyl)amine;
N-(8-chloro-dibenz|b,f|oxepin-10-ylmethyl)-N,N-dimethylamine and
N-(8-chloro-dibenz|b,f|oxepin-10-ylmethyl)-N,N-diethylamine and of pharmaceutically acceptable salts thereof, and also to N-(dibenz|b,f|oxepin-10-ylmethyl)-N-methyl-N-prop-2-ynylamine;
N-allyl-N-(dibenz|b,f|oxepin-10-ylmethyl)amine;
N-allyl-N-(dibenz|b,f|oxepin-10-ylmethyl)-N-methylamine;
N-(dibenz|b,f|oxepin-10-ylmethyl)amine;
N-(dibenz|b,f|oxepin-10-ylmethyl)-N-prop-2-ynylamine;
N-(dibenz|b,f|oxepin-10-ylmethyl)-N-propylamine;
N-(dibenz|b,f|oxepin-10-ylmethyl)-N-methyl-N-propylamine;
1-dibenz[b,f]oxepin-10-ylmethyl-piperidine;
4-dibenz[b,f]oxepin-10-ylmethyl-morpholine;
N-(1-chloro-dibenz[b,f]oxepin-10-ylmethyl)-N-methyl-N-prop-2-ynylamine;
1-(1-chloro-dibenz|b,f|oxepin-10-ylmethyl)-pyrrolidine;
N-(1-chloro-dibenz|b,f|oxepin-10-ylmethyl)-N-methyl-N-propylamine;
N-methyl-N-prop-2-ynyl-N-(3-trifluoromethyl-dibenz|b,f|oxepin-10-ylmethyl)amine;
1-(3-trifluoromethyl-dibenz[b,f|oxepin-10-ylmethyl)-pyrrolidine;
N-(7-chloro-dibenz|b,f|oxepin-10-ylmethyl)-N-methyl-N-prop-2-ynylamine;
1-(7-chloro-dibenz|b,f|oxepin-10-ylmethyl)-pyrrolidine;
N-(8-methoxy-dibenz|b,f|oxepin-10-ylmethyl)-N-methyl-N-prop-2-ynylamine;
N-(8-tert-butyl-dibenz[b,f|oxepin-10-ylmethyl)-N-methyl-N-prop-2-ynylamine;
1-(8-tert-butyl-dibenz[b,f|oxepin-10-ylmethyl)-pyrrolidine;
N-(6-chloro-dibenz|b,f|oxepin-10-ylmethyl)-N-methyl-N-prop-2-ynylamine;
1-(6-chloro-dibenz|b,f|oxepin-10-ylmethyl)pyrrolidine;
N-(1-fluoro-dibenz[b,f|oxepin-10-ylmethyl)-N-methyl-N-prop-2-ynylamine;
1-(1-fluoro-dibenz|b,f|oxepin-10-ylmethyl)pyrrolidine;
N-benzyl-N-(dibenz|b,f|oxepin-10-ylmethyl)amine;
N-benzyl-N-(dibenz|b,f|oxepin-10-ylmethyl)-N-methylamine;
N-(dibenz|b,f|oxepin-10-ylmethyl)-N-propyl-N-benzylamine and
N-allyl-N-benzyl-N-(dibenz|b,f|oxepin-10-ylmethyl)amine themselves, to processes for the preparation thereof and to pharmaceutical compositions comprising them.

The process for the preparation of novel compounds of formula I comprises a) condensing a compound of formula II

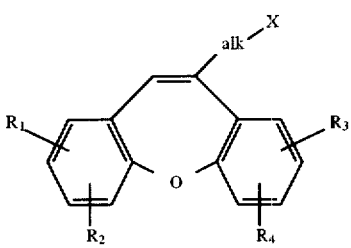

with a compound of formula III

Y—R       (III)

wherein one of the radicals X and Y is reactive esterified hydroxy and the other is free or temporarily protected amino, and R, $R_1$, $R_2$, $R_3$ and $R_4$ are as defined hereinbefore, and removing again the amino-protecting group that may have been temporarily introduced, or b) in a compound of formula IV

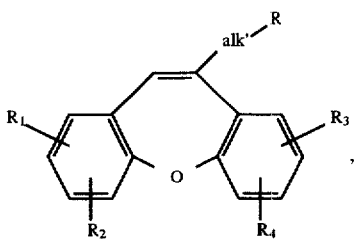

wherein alk' is a lower alkylene group substituted by oxo or by free or esterified hydroxy, reducing the group alk' with replacement of the oxygen function to form the corresponding group alk and, if desired, in each case converting a compound obtainable in accordance with the process into a different compound of formula I, separating a mixture of isomers obtainable in accordance with the process into its components and isolating the desired isomer, and/or converting a salt obtainable in accordance with the process into the free compound or converting a free compound obtainable in accordance with the process into a salt.

Reactive esterified hydroxy in starting materials of formulae II and III in accordance with process variant a) is, for example, hydroxy esterified with a hydrohalic acid or an organic sulfonic acid, such as halogen, for example chlorine, bromine or iodine, or unsubstituted or lower-alkyl-, halo- and/or nitro-substituted benzenesulfonyloxy, such as benzenesulfonyloxy, p-bromobenzenesulfonyloxy or p-toluenesulfonyloxy, or lower alkanesulfonyloxy, such as methanesulfonyloxy.

The reaction of compounds of formulae II and III is carried out in customary manner, for example in the presence of a basic condensing agent, such as a tertiary or sterically hindered binary organic nitrogen base, such as a tri-lower alkylamine or sterically hindered di-lower alkylamine, such as triethylamine or diisopropylamine, or a heteroaromatic base, such as pyridine or dimethylaminopyridine, advantageously in an organic solvent, such as toluene, and, if necessary, with cooling or heating, for example in a temperature range of from approximately 0° to approximately 80° C.

Suitable amino-protecting groups for the intermediate protection of primary amino groups are customary amino-protecting groups, especially amino-protecting groups that can be removed by solvolysis. Such groups are, for example, acyl groups derived from a carboxylic acid or from a semi-ester of carbonic acid, such as unsubstituted or halogenated lower alkanoyl, for example lower alkanoyl, such as formyl, acetyl or pivaloyl, polyhalo-lower alkanoyl, such as trifluoroacetyl, lower alkoxycarbonyl, such as methoxycarbonyl, ethoxycarbonyl, isopropyloxycarbonyl or tert-butyloxycarbonyl, or unsubstituted or substituted phenyl-lower alkoxycarbonyl, such as benzyloxycarbonyl, and also silyl groups, such as tri-lower alkylsilyl, for example trimethylsilyl.

The removal of those amino-protecting groups is carried out in customary manner, for example by treatment with a solvolysis agent, such as water in the presence of an acid, for example an aqueous mineral acid, such as a hydrohalic acid, or an alkali metal hydroxide, such as sodium hydroxide solution or potassium hydroxide solution or, especially for the removal of tri-lower alkoxycarbonyl, a sulfonic acid, such as methanesulfonic acid in a halogenated hydrocarbon, such as dichloromethane, or, especially for the removal of formyl, a suitable silyl compound, such as a tri-lower alkylsilyl halide, such as trimethylsilyl bromide, or a disilazane, such as hexamethyldisilazane.

The starting materials of formulae II and III are known or can be prepared analogously to the method of preparation of known compounds of formulae II and III.

For example, compounds of formula II wherein alk is methylene and X is reactively esterified hydroxy are obtained, for example, as follows: compounds of formulae V and VI

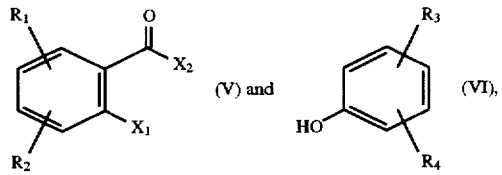

wherein $X_1$ is halogen and $X_2$ is hydrogen or hydroxy, are condensed with one another in customary manner, the condensation being carried out preferably in a temperature range of from approximately 100° C. to approximately 180° C. and, when using as starting materials compounds of formula V wherein $X_2$ is hydroxy and $X_1$ is, for example, chlorine, preferably in the presence of copper/copper(I) iodide and, when using as starting materials compounds of formula V wherein $X_2$ is hydrogen and $X_1$ is, for example, fluorine, preferably in the presence of potassium carbonate in dimethylacetamide, the group —C(=P)—$X_1$ in a resulting compound of formula VII

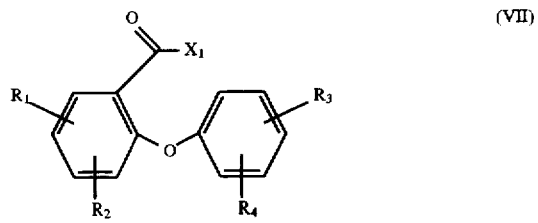

is reduced to hydroxymethyl in customary manner, for example by treatment with a di-light metal hydride, such as lithium aluminium hydride in tetrahydrofuran, the hydroxymethyl group is converted into halomethyl in customary manner, for example by heating with a hydrohalic acid, especially hydrobromic acid, the halogen atom is replaced by cyano in customary manner, for example by treatment with an alkali metal cyanide, such as sodium cyanide in ethanol, and the resulting compound of formula VIII

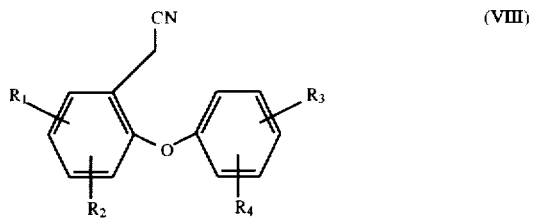

is reacted in customary manner, for example in the presence of an alkali metal alkanolate, such as sodium methanolate, with an oxalic acid di-lower alkyl ester, for example diethyl oxalate, worked up under acidic conditions, and the carboxy group in the resulting compound of formula IX

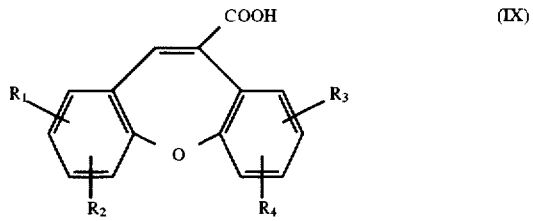

is reduced to hydroxymethyl in customary manner, for example by treatment with a haloformic acid ester, such as isobutyl chloroformate, in the presence of a nitrogen base, such as N-methylmorpholine, preferably in an ethereal solvent, such as dimethoxymethane, and then with a di-light metal hydride, such as sodium borohydride in water, and the resulting compound of formula X

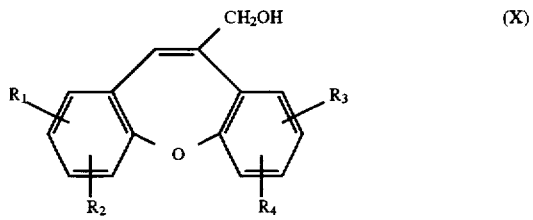

is treated with an agent that introduces the group X, such as a hydrohalic acid or a sulfonyl of halide, such as methane-sulfonyl chloride.

Higher homologues of compounds of formula II wherein alk is ethylene, propylene etc. or ethylidene, propylidene etc. may be obtained by, for example, at the stage of the acid IX, either carrying out a chain lengthening in customary manner or converting the carboxy group into the desired 1-oxoalkyl group in customary manner.

Compounds of formula II wherein X is free or protected amino can be obtained, for example, from the reactive esters obtained as described above, by customary saturated solution of ammonia in methanol and, if desired, subsequent introduction of the amino-protecting group in customary manner.

In starting materials of formula IV according to process variant b), esterified hydroxy is, for example, hydroxy esterified with a carboxylic acid or with a semiester of carbonic acid, such as unsubstituted or halogenated lower alkanoyloxy, for example lower alkanoyloxy, such as formyloxy, acetyloxy or pivaloyloxy, lower alkoxycarbonyloxy, such as methoxycarbonyloxy, ethoxycarbonyloxy, isopropyloxycarbonyloxy or tert-butyloxycarbonyloxy, or unsubstituted or substituted phenyl-lower alkoxycarbonyloxy, such as benzyloxycarbonyloxy.

The reduction of compounds of formula IV is carried out in customary manner, for example pie by treatment with a di-light metal hydride, such as lithium aluminium hydride in tetrahydrofuran.

Starting materials of formula IV wherein alk' is ω-oxo-lower alkyl bonded to the group R in the ω-position can be obtained, for example, from the corresponding acids of formula IX or the homologues thereof by reaction with an amine of formula III, wherein Y is free or temporarily protected amino, in customary manner, for example by treatment with an acid halogenating agent, such as oxalyl chloride in the presence of dimethylformamide. It is then possible from those starting materials, by means of partial reduction and, if desired, esterification, to obtain the corresponding compounds of formula IV wherein alk' is lower alkylene substituted by free or esterified hydroxy. Starting materials of formula IV wherein alk' is (ω-1)-oxo-lower alkyl bonded to the group R in the of position can be obtained, for example, from the corresponding methyl ketones by halogenation, for example by means of N-bromo- or N-chloro-succinimide, and subsequent reaction with an amine of formula II wherein Y is free or temporarily protected amino.

Compounds obtainable in accordance with the process may be converted in customary manner into different compounds of formula I.

For example, in compounds of formula I wherein R is unsubstituted amino, the amino group may be substituted in customary manner by one or two identical or different monovalent aliphatic or araliphatic radicals or by a divalent aliphatic radical. In an analogous manner, it is also possible in compounds of formula I wherein R is amino substituted by a monovalent aliphatic or araliphatic radical to introduce a further monovalent aliphatic or araliphatic radical.

Resulting salts may be converted in a manner known per se into the free compounds, for example by treatment with a base, such as an alkali metal hydroxide, a metal carbonate or hydrogen carbonate, or with another salt-forming base mentioned at the beginning or with an acid, such as a mineral acid, for example hydrochloric acid, or another salt-forming acid mentioned at the beginning.

Resulting salts may be converted in a manner known per se into different salts, for example acid addition salts may be converted by treatment with a suitable metal salt, such as a sodium, barium or silver salt, of a different acid, in a suitable solvent in which an inorganic salt that forms is insoluble and is thus eliminated from the reaction equilibrium, and basic salts may be converted into different salts by freeing the free acid and converting into a salt again.

The compounds of formula I, including their salts, may also be obtained in the form of hydrates, or may include the solvent used for their crystallisation.

In view of the close relationship between the novel compounds in free form and in the form of their salts, hereinbefore and hereinafter any reference to the free compounds and their salts should be understood as including optionally also the corresponding salts and free compounds, respectively, as appropriate and expedient.

Resulting mixtures of diastereoisomers and mixtures of racemates can be separated in known manner into the pure diastereoisomers and racemates on the basis of the physico-chemical differences between the constituents, for example by chromatography and/or fractional crystallisation. Resulting racemates can also be separated into the optical antipodes by known methods, for example by recrystallisation from an optically active solvent, with the aid of microorganisms or by reaction of the resulting mixture of diastereoisomers or racemate with an optically active auxiliary compound, for example according to the acidic, basic or functionally modifiable groups present in compounds of formula I with an optically active acid, base or an optically active alcohol, to form mixtures of diastereoisomeric salts or functional derivatives, such as esters, and separation thereof into the diastereoisomers from which the desired enantiomer can be freed in the appropriate customary manner. Examples of suitable bases, acids and alcohols are optically active alkaloid bases, such as strychnine, cinchonine or brucine, or D- or L-(1-phenyl)ethylamine, 3-pipecoline, ephedrine, amphetamine and similar synthetically obtainable bases, optically active carboxylic or sulfonic acids, such as quinic acid or D- or L-tartaric acid, D- or L-di-o-toluoyltartaric acid, D- or L-malic acid, D- or L-mandelic acid or D- or L-camphorsulfonic acid, or optically active alcohols, such as borneol or D- or L-(1-phenyl)ethanol.

The invention relates also to those forms of the process in which a compound obtainable as intermediate at any stage of the process is used as starting material and the remaining steps are carried out, or in which a starting material is used in the form of a salt or, especially, is formed under the reaction conditions.

The invention relates also to the novel starting materials developed specifically for the preparation of the compounds of the invention, especially to those starting materials resulting in the compounds of formula I that were described at the beginning as being preferred, to processes for the preparation thereof and to their use as intermediates.

This relates, for example, to amides of formula IV wherein alk' is ω-oxo-lower alkyl bonded to the group R in the ω-position, especially carbonyl, and to salts thereof, as well as to processes for the preparation thereof.

The invention accordingly relates also to novel compounds of formula IVa

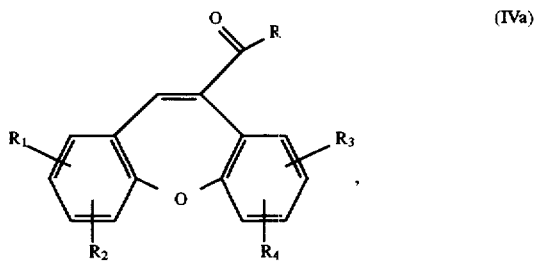

(IVa)

wherein

R is an amino group that is unsubstituted or mono- or di-substituted by monovalent aliphatic and/or araliphatic radicals or disubstituted by divalent aliphatic radicals and $R_1$, $R_2$, $R_3$ and $R_4$ are each, independently of the others, hydrogen, lower alkyl, lower alkoxy, halogen or trifluoromethyl, and to salts thereof as well as to processes for the preparation thereof.

The invention relates preferably to those compounds of formula IVa resulting in the compounds of formula I that were described at the beginning as being preferred, and to salts thereof as well as to processes for the preparation thereof.

The process for the preparation of novel compounds of formula IVa comprises reacting a compound of formula IX

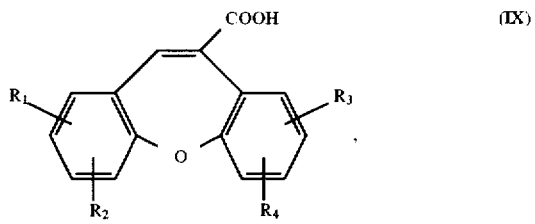

(IX)

wherein R, $R_1$, $R_2$, $R_3$ and $R_4$ are as defined hereinbefore, with an amine of formula III

Y—R        (III), wherein Y is free or temporarily protected amino, to form the corresponding amide, removing again the amino-protecting group that may have been temporarily introduced and, if desired, in each case converting a compound obtainable in accordance with the process into a different compound of formula I, separating a mixture of isomers obtainable in accordance with the process into its components and isolating the desired isomer and/or converting a salt obtainable in accordance with the process into the free compound or a free compound obtainable in accordance with the process into a salt.

The reaction of compounds of formula IVa to form the corresponding amides is carried out in customary manner, for example by treatment with an acid halogenating agent, such as oxalyl chloride in the presence of dimethylformamide.

The invention also relates preferably to pharmaceutical compositions comprising the compounds of formula I according to the invention or pharmaceutically acceptable salts thereof as active ingredients, and to processes for the preparation thereof.

The pharmaceutical compositions according to the invention, which comprise a compound according to the invention or a pharmaceutically acceptable salt thereof, are pharmaceutical compositions for enteral, such as oral or rectal, and parenteral administration to warm-blooded animal(s) that comprise the pharmacological active ingredient alone or together with a pharmaceutically acceptable carrier. The daily dose of the active ingredient depends on the age and the individual condition as well as on the mode of administration.

The novel pharmaceutical compositions comprise, for example, from approximately 10% to approximately 80%, preferably from approximately 20% to approximately 60%, active ingredient. Pharmaceutical compositions according to the invention for enteral or parenteral administration are, for example, in unit dose form, such as in the form of dragees, tablets, capsules or suppositories, and also ampoules. They are prepared in a manner known per se, for example by means of conventional mixing, granulating, confectioning, dissolving or lyophilising processes. For example, pharmaceutical compositions for oral administration can be obtained by combining the active ingredient with solid carriers, if desired granulating a resulting mixture, and processing the mixture or granules, if desired or necessary, after the addition of appropriate excipients, into tablets or dragee cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose and/or polyvinylpyrrolidone, if desired disintegrators, such as the above-mentioned starches, also carboxymethyl starch, crosslinked polyvinylpyrrolidone, agar, alginic acid or a salt thereof, such as sodium alginate. Excipients are especially flow agents, flow conditioners and lubricants, for example silicic acid, talc, stearic acid or salts thereof, such as magnesium or calcium stearate, and/or polyethylene glycol. Dragee cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or dragee coatings, for example for identification purposes or to indicate different doses of active ingredient.

Other orally administrable pharmaceutical compositions are hard gelatin capsules and also soft, sealed capsules made of gelatin and a plasticiser, such as glycerol or sorbitol. The is hard gelatin capsules may comprise the active ingredient in the form of granules, for example in admixture with fillers, such as lactose, binders, such as starches, and/or glidants, such as talc or magnesium stearate, and if desired with stabilisers. In soft capsules the active ingredient is preferably dissolved or suspended in suitable liquids, such as fatty oils, paraffin oil or liquid polyethylene glycols, it likewise being possible for stabilisers to be added.

Suitable rectally administrable pharmaceutical compositions are, for example, suppositories that consist of a combination of the active ingredient with a suppository base material. Suitable suppository base materials are, for example, natural or synthetic triglycerides, paraffin hydrocarbons, polyethylene glycols or higher alkanols. Gelatin rectal capsules that comprise a combination of the active ingredient with a base material may also be used. Suitable base materials include, for example, liquid triglycerides, polyethylene glycols and paraffin hydrocarbons.

There are suitable for parenteral administration by infusion and/or injection especially aqueous solutions of an active ingredient in water-soluble form, for example in the form of a water-soluble salt, and also suspensions of the active ingredient, such as corresponding oily suspensions, there being used suitable lipophilic solvents or vehicles, such as fatty oils, for example sesame oil, or synthetic fatty acid esters, for example ethyl oleate or triglycerides, or aqueous suspensions that comprise viscosity-increasing substances, for example sodium carboxymethylcellulose, sorbitol and/or dextran, and optionally also stabilisers.

The dosage of the active ingredient depends on the species of warm-blooded animal, the age and the individual condition and also on the mode of administration. Normally the estimated approximate daily dose in the case of oral administration to a patient weighing approximately 75 kg is from approximately 10 mg to approximately 500 mg.

The following Examples serve to illustrate the invention; temperatures are given in degrees Celsius and pressures in mbar.

EXAMPLE 1

N-(Dibenz[b,f]oxepin-10-ylmethyl-N-methyl-N-prop-2-ynylamine

Methylpropargylamine (4.5 g, 65 mmol) is dissolved in benzene (75 ml) and methanol (25 ml). At 40° C. a solution of 10-bromomethyldibenz[b,f]oxepine (7.0 g, 25 mmol) in benzene (25 ml) is added dropwise in the course of half an hour. When the addition is complete, the mixture is stirred for a further half hour at 40°–50° C., poured into water, washed three times with water and then extracted with 5% methanesulfonic acid. The acidic aqueous phase is rendered basic with concentrated ammonia and extracted with diethyl ether. The ethereal phase is dried over sodium sulfate and concentrated by evaporation. Crystallisation of the residue from petroleum ether yields N-(dibenz[b,f]oxepin-10-ylmethyl-N-methyl-N-prop-2-ynylamine alias 10-(N-propargyl-N-methyl-amino)methyldibenz[b,f]oxepine (5.3 g, 77%).

Melting point: 66°–67° C.

EXAMPLE 2

N-Allyl-N-(dibenz[b,f]oxepin-10-ylmethyl)amine hydrochloride

At 50° C. a solution at of 0.5 ml (1.74 mmol) of 10-bromomethyl-dibenz[b,f]oxepine is squirted into a solution of 0.3 ml (4 mmol) of allylamine in 0.9 ml of anhydrous methanol and the mixture is stirred for 30 minutes. Tert-butyl methyl ether and ethyl acetate are added and the mixture is extracted 3× with 20 ml of 1N hydrochloric acid each time, the combined aqueous phases are rendered basic with potassium hydroxide pellets and extracted 2× with ethyl acetate, and the organic phases are dried over sodium sulfate and concentrated. 0.35 ml (0.7 mmol) of 2N ethereal hydrochloric acid is added to the crude amine (180 mg) in 2 ml of diethyl ether, and the precipitated white hydrochloride is washed with diethyl ether and dried under a high vacuum at 40° C. 200 mg (667 µmol) =39% of the title compound alias 10-allylaminomethyldibenz[b,f]oxepine are obtained in the form of white crystals; melting point: 148°–158° C.; $^1$H-NMR (CD$_3$OD, 200 MHz): 3.74 (d, 2H); 4.35 (d, 2H); 5.55 (m, 2H); 5.95 (m, 1H); 7.20–7.58 (m, 9H); MS: 263 (M$^+$, free base), 222, 208, 181, 165, 152.

EXAMPLE 3

N-Ally-N-(dibenz[b,f]oxepin-10-ylmethyl)-N-methylamine hydrochloride

Preparation analogous to Example 2 from 10-bromomethyl-dibenz[b,f]oxepine and N-methyl-allylamine. Yield: 71%; melting point: 153°–156° C.; $^1$H-NMR (CD$_3$OD, 200 MHz): 2.85 (s, 3H); 3.86 (d, 2H); 4.50 (sbr, 2H); 5.60 (d, 1H); 5.68 (s, 1H); 6.00 (m, 1H); 7.20–7.60 (m, 9H); MS: 277 (M$^+$, free base), 208, 181, 152.

EXAMPLE 4

N-(Dibenz[b,f]oxepin-10-ylmethyl-N-methyl-N-prop-2-ynylamine

Preparation analogous to Example 2 from 10-bromomethyl-dibenz[b,f]oxepine and N-methyl-N-propargylamine, as free base, chromatographed on silica gel with hexane/ethyl acetate=4:1 and crystallised from a small amount of petroleum ether. Yield: 74%; melting point: 67°–68° C.; $^1$H-NMR (CDCl$_3$, 300 MHz): 2.30 (d, 1H); 2.42 (s, 3H); 3.48 (t, 2H); 6.90 (d, 1H); 7.08–7.36 (m, 7H); 7.56 (m, 1H); MS: 275 (M$^{30}$), 232, 208, 181, 165, 152; analysis: C 82.77% (82.88); H 6.18% (6.22); N 4.99% (5.09).

The title compound is identical to the product according to Example 1.

EXAMPLE 5

N-(Dibenz[b,f]oxepin-10-ylmethyl-N-methyl-N-prop-2-ynylamine oxalate

Preparation analogous to Example 2; oxalate salt from free base with oxalic acid in ethanol.

19

Melting point: 202°–205° C.; analysis: C 68.79% (69.03); H 5.29% (5.24); N 3.86% (3.83).

EXAMPLE 6

N-(Dibenz|b.f|oxepin-10-ylmethyl)amine
(in the form of the hydrochloride)

1.0 g (3.48 mmol) of 10-bromomethyl-dibenz|b.f|oxepine in 3 ml of toluene is added dropwise at 40° C. to 30 ml of NH$_3$-saturated methanol and the mixture is stirred at 35°–50° C. for 1 hour and at room temperature overnight. The solvent is partially removed, and the reaction mixture is taken up in tert-butyl methyl ether, washed with 0.1N sodium hydroxide solution and extracted with 1N hydrochloric acid. The aqueous phase is rendered basic with sodium hydroxide pellets and extracted with tert-butyl methyl ether, the organic phase is dried over sodium sulfate and the solvent is removed. 349 mg (1.56 mmol)=45% of N-(dibenz|b.f|oxepin-10-ylmethyl)amine are obtained in the form of a light-yellow oil; TLC (silica gel; ethyl acetate; UV): R$_f$=0.09.

EXAMPLE 7

N-(Dibenz|b.f|oxepin-10-ylmethyl)-N-prop-2-ynylamine hydrochloride

A mixture of 1.1 g (3.044 mmol) of N-(dibenz|b.f|oxepin-10-ylmethyl-prop-2-ynyl-carbamic acid tert-butyl ester and 1.45 ml of methanesulfonic acid in 1 ml of dioxane and 9 ml of dichloromethane is stirred for 1 hour at room temperature. 2N sodium hydroxide solution is added and the mixture is extracted 2× with dichloromethane. The organic phase is concentrated using a rotary evaporator, taken up in ethyl acetate and extracted 3× with 1N hydrochloric acid, and the aqueous phase is rendered basic with potassium hydroxide pellets, extracted 3× with dichloromethane, dried over sodium sulfate and concentrated. The crude light-brown oil is dissolved in 2N ethereal hydrochloric acid and concentrated. The crude hydrochloride (beige crystals) is recrystallised from ethyl acetate/methanol. 386 mg (1.30 mmol)= 42% of N-(dibenz|b.f|oxepin-10-ylmethyl)-N-prop-2-ynylamine hydrochloride alias 10-propargylaminomethyldibenz|b.f|oxepine hydrochloride are obtained in the form of white crystals; melting point: 181°–183° C.; MS: 261 (M$^+$, free base), 222,181, 165, 152.

The starting material can be prepared, for example, in the following manner:

a) Dibenz|b.f|oxepin-10-ylmethyl-carbamic acid tert-butyl ester 2.25 g (10.3 mmol) of di-tert-butyl dicarbonate (BOC)$_2$O are added at room temperature to a solution of 2.3 g (10.3 mmol) of N-(dibenz|b.f|oxepin-10-ylmethyl)amine in 20 ml of dichloromethane, and the mixture is stirred for 30 minutes and freed of solvent using a rotary evaporator. 3.61 g of dibenz|b.f|oxepin-10-ylmethyl-carbamic acid tert-butyl ester are obtained in the form of a crude yellow oil which becomes solid on being left to stand. TLC (silica gel; ethyl acetate/hexane=9:1; UV): R$_f$=0.36.

b) Dibenz|b.f|oxepin-10-ylmethyl-prop-2-ynyl-carbamic acid tert-butyl ester 1.0 9 (3.091 mmol) of dibenz(b.f|oxepin-10-ylmethyl-carbamic acid tert-butyl ester is placed in 10 ml of dimethylformamide, 0.22 g (4.636 mmol) of 55% sodium hydride suspension (in oil) is added at room temperature, the mixture is stirred for 15 minutes and then 0.279 ml (3.709 mmol) of propargyl bromide is added dropwise at room temperature. After 1 hour, water and a small amount of brine are carefully added and tert-butyl methyl ether is mixed in.

20

The organic phase is washed 4× with water, dried over sodium sulfate and concentrated. 1.106 g (3.06 mmol)= 98.8% of dibenz|b.f|oxepin-10-ylmethyl-prop-2-ynyl-carbamic acid tert-butyl ester are obtained in the form of a brown oil; TLC (silica gel; ethyl acetate/hexane=9:1; UV): R$_f$=0.45.

EXAMPLE 8

N-(Dibenz|b.f|oxepin-10-ylmethyl)-N-propylamine hydrochloride

Preparation analogous to Example 2 from 10-bromomethyl-dibenz|b.f|oxepine and propylamine; yield: 19%; melting point: 142°–152° C.; $^1$H-NMR (CD$_3$OD, 200 MHz): 1.01 (t, 3H); 1.76 (m, 2H); 3.03 (m, 2H); 4.25 (s, 2H); 7.19–7.69 (m, 10H); MS: 265 (M$^+$, free base), 222, 207, 181.

EXAMPLE 9

N-(Dibenz|b.f|oxepin-10-ylmethyl)-N-methyl-N-propylamine tosylate

Preparation analogous to Example 2 from 10-bromomethyl-dibenz|b.f|oxepine and N-methyl-N-propylamine. Tosylate prepared with 1 equivalent of p-toluenesulfonic acid in ethyl acetate, crystallised from dichloromethane/tert-butyl methyl ether. Yield: 68%; melting point: 179°–180° C.; $^1$H-NMR (CD$_3$OD, 200 MHz): 0.97 (t, 3H); 1.78 (m, 2H); 2.36 (s, 3H); 3.15 (mbr, 2H); 4.50 (mbr, 2H); 7.17–7.75 (m, ca. 13H); MS: 279 (M$^+$, free base), 250, 207.

EXAMPLE 10

1-Dibenz|b.f|oxepin-10-ylmethyl-piperidine hydrochloride

A solution of 1.954 9 (6.395 mmol) of dibenz|b.f|oxepin-10-yl-piperidin-1-yl-methanone in 5 ml of tetrahydrofuran is added dropwise at 0° C. to a suspension of 365 mg (9.59 mmol) of lithium aluminium hydride in 15 ml of tetrahydrofuran and the mixture is then stirred at room temperature overnight. The mixture is hydrolysed with 0.37 ml of water, 4N sodium hydroxide and 1.11 ml of water, filtered, and the filtrate is extracted with ethyl acetate. The resulting greenish oil is converted with ethereal hydrochloric acid into the hydrochloride which is recrystallised from hexane and a very small amount of tert-butyl methyl ether to yield 1.29 g (3.93 mmol)=61% of 1-dibenz|b.f|oxepin-10-ylmethyl-piperidine hydrochloride in the form of white crystals; melting point: 172°–173° C.; $^1$H-NMR (CD$_3$OD, 200 MHz): 1.40–2.00 (mbr, 6H); 3.00 (tbr, 2H); 3.52 (dbr, 2H); 4.47 (s, 2H); 7.26–7.63 (m, 9H); MS: 291 (M$^+$, free base), 208, 181, 152.

The starting material can be prepared, for example, in the following manner:

a) Dibenz|b.f|oxepin-10-yl-piperidin-1-yl-methanone 1.1 ml (12.59 mmol) of oxalyl chloride and 1 drop of dimethylformamide are added at room temperature to a solution of 3.0 g is (12.59 mmol) of dibenz|b.f|oxepine-10-carboxylic acid in 20 ml of dichloromethane and the mixture is stirred for 4 hours. 1.86 ml (18.88 mmol) of piperidine and 2.62 ml (18.88 mmol) of Et$_3$N are then added and the mixture is stirred at room temperature overnight. The reaction mixture is washed 1× with hydrochloric acid and brine, and the organic phase is dried, concentrated, subjected to column chromatography and crystallised from tert-butyl methyl ether. 2.64 g (8.6 mmol)=69% of dibenz|b.f|oxepin-10-yl-piperidin-1-yl-methanone are obtained in the form of light-yellow crystals; melting point: 127°–128° C.; $^1$H-NMR (CDCl$_3$, 200 MHz): 1.30–1.50 (mbr, 2H); 1.50–1.70 (mbr, 4H); 3.30–3.45 (mbr, 2H); 3.63–3.78 (mbr 2H); 6.92 (s, 1H); 7.10–7.40 (m, 8H); MS: 305 (M$^+$), 221, 193, 165; TLC (silica gel; ethyl acetate/hexane=1:1; UV): R$_f$=0.32.

EXAMPLE 11

4-Dibenz|b.f|oxepin-10-ylmethyl-morpholine hydrochloride

Preparation analogous to Example 10 from dibenz|b.f|oxepin-10-yl-morpholin-4-yl-methanone; yield: 62%; white crystals; melting point: 213°–215° C.; $^1$H-NMR (CDCl$_3$, 300 MHz): 2.95 (m, 2H); 3.32 (m(d), 2H); 3.90 (m(d), 2H); 4.25 (t, 2H); 4.40 (s, 2H); 7.11–7.45 (m, 9H). MS: 293 (M$^+$, free base), 208, 181, 152.

The starting material can be prepared, for example, in the following manner:

a) Dibenz|b.f|oxepin-10-yl-morpholin-4-yl-methanone

Preparation analogous to Example 10a from dibenz|b.f|oxepine-10-carboxylic acid and morpholine; yield: 62%; yellow oil; $^1$H-NMR (CDCl$_3$, 200 MHz): 3.30 (mbr, 4H); 3.62 (mbr, 4H); 6.90–7.28 (m, 9H); MS: 307 (M$^+$), 221, 193, 165; TLC (silica gel; ethyl acetate/hexane=1:1; UV): R$_f$=0.17.

EXAMPLE 12

N-(1-Chloro-dibenz|b.f|oxepin-10-ylmethyl)-N-methyl-N-prop-2-ynylamine hydrochloride Preparation analogous to Example 2 from 10-bromomethyl-1-chloro-dibenz|b.f|oxepine with N-methyl-N-propargylamine. Yield: 75%; melting point: not determined, (white foam); $^1$H-NMR (CDCl$_3$, 200 MHz): 2.35 (t, 1H); 2.45 (s, 3H); 3.51 (d, 2H); 3.70 (s, 2H); 7.10–7.40 (m, 7H); 7.61 (m, 1H).

The starting material can be prepared, for example, in the following manner:

a) 2-Chloro-6-phenoxy-benzaldehyde

A mixture of 15.8 g (100 mmol) of 2-chloro-6-fluorobenzaldehyde, 9.4 g (100 mmol) of phenol and 20.7 g (150 mmol) of potassium carbonate in 150 ml of dimethylacetamide is heated under reflux for 4 hours. The mixture is allowed to cool, water is added and the mixture is extracted 3× with tert-butyl methyl ether. The organic phases are washed with 2N sodium hydroxide solution and brine, dried over sodium sulfate and concentrated. Bulb tube distillation (175° C., 0.04 mbar) yields 19.46 g (83.64 mmol)=83.6% of 2-chloro-6-phenoxy-benzaldehyde in the form of a yellow oil; $^1$H-NMR (CDCl$_3$, 200 MHz): 6.75–7.45 (m, 8H); 10.58 (s, 1H).

b) (2-Chloro-6-phenoxy-phenyl)methanol 19.0 g (77.67 mmol) of 2-chloro-6-phenoxy-benzaldehyde in approximately 40 ml of tetrahydrofuran are added dropwise at room temperature in the course of 30 minutes to a suspension of 4.42 g (116.5 mmol) of lithium aluminium hydride in approximately 150 ml of tetrahydrofuran. The mixture is then heated under reflux for 4 hours, cooled and hydrolysed with 4.4 ml of water, 4.4 ml of 4N sodium hydroxide and 13.2 ml of water. The reaction mixture is boiled under reflux for 30 minutes, cooled and filtered, and the suction filter residue is 3× taken up in ethyl acetate, boiled under reflux for 15 minutes and filtered. The combined filtrates are concentrated. 17.97 g (76.57 mmol) =94% of crude (2-chloro-6-phenoxy-phenyl)-methanol are obtained in the form of a yellow oil; TLC (silica gel; ethyl acetate/hexane=1:1; UV): R$_f$=0.68; $^1$H-NMR (CDCl$_3$, 200 MHz): 4.90 (s, 2H); 6.76–7.40 (m, 8H).

c) (2-Chloro-6-phenoxy-phenyl)-bromomethane 17.5 g (70.94 mmol) of (2-chloro-6-phenoxy-phenyl)-methanol are heated under reflux for 3 hours in 150 ml of 48% hydrobromic acid. The mixture is cooled, water is added and the mixture is extracted 3× with ethyl acetate. The organic phases are washed with brine, dried over sodium sulfate and concentrated. 21.21 g (>1 00%) of crude (2-chloro-6-phenoxy-phenyl)-bromomethane are obtained in the form of a yellow oil; TLC (silica gel; ethyl acetate/hexane=1:1; UV): R$_f$=0.70; $^1$H-NMR (CDCl$_3$, 200 MHz): 4.78 (s, 2H); 6.70–7.41 (m, 8H).

d) (2-Chloro-6-phenoxy-phenyl)acetonitrile

A solution of 21.0 g (70.57 mmol) of (2-chloro-6-phenoxy-phenyl)-bromomethane in 16.5 ml of ethanol is added dropwise at 80° C. to a solution of 4.5 g (91.74 mmol) of sodium cyanide in 9.2 ml of water and 2.3 ml of ethanol and the reaction mixture is boiled under reflux for 4 hours. After cooling, the mixture is concentrated using a rotary evaporator, the residue is taken up in ethyl acetate and the organic phase is washed 2× with water and 1× with brine, dried over sodium sulfate, concentrated and chromatographed on silica gel with ethyl acetate to yield 10.82 g (44.40 mmol)=63% of (2-chloro-6-phenoxyphenyl)-acetonitrile in the form of a brown oil; TLC (silica gel; ethyl acetate; UV): R$_f$=0.42; $^1$H-NMR (CDCl$_3$, 200 MHz): 3.96 (s, 2H); 6.74–7.46 (m, 8H).

e) 1-Chloro-dibenz|b.f|oxepine-10-carboxylic acid 10.82 g (44.40 mmol) of (2-chloro-6-phenoxy-phenyl)-acetonitrile and 7.85 g (53.72 mmol) of oxalic acid diethyl ester are added at room temperature to a freshly prepared sodium ethanolate solution (1.5 g (53.72 mmol) of sodium in 50 ml of ethanol) and the mixture is stirred for 18 hours. The mixture is rendered acidic with 1N hydrochloric acid, concentrated using a rotary evaporator and extracted 2× with ethyl acetate, and the organic phase is washed with brine, dried over sodium sulfate and concentrated to yield 15.99 g of crude intermediate (3-(2-chloro-6-phenoxy-phenyl)-2-hydroxy-4-nitrilo-but-2-enoic acid ethyl ester). 15.0 g (approximately 43.6 mmol) of the above intermediate are placed in 105 ml of glacial acetic acid and stirred for 20 minutes, 51.9 ml of water and 51.9 ml of sulfuric acid are slowly added, and the mixture is heated for 4 hours under reflux and then for 18 hours at room temperature. The reaction mixture is extracted with ethyl acetate, the organic phase is washed with water and 3× with 4N sodium hydroxide, and the aqueous phase is extracted 1× with ethyl acetate. The aqueous phases are rendered acidic with concentrated hydrochloric acid and extracted 3× with ethyl acetate, and the organic phase is dried over sodium sulfate and concentrated. 7.71 g (28.27 mmol)=60.3% of 1-chloro-dibenz|b.f|oxepine-10-carboxylic acid are obtained in the form of a yellow solid; TLC (silica gel; ethyl acetate/hexane=1:1; UV): R$_f$=0.21; $^1$H-NMR (CDCl$_3$, 200 MHz): 7.15–7.47 (m, 7H); 7.68 (m, 1H); 8.39 (s, 1H).

f) (1-Chloro-dibenz|b.f|oxepin-10-yl)methanol 2.0 ml (18.33 mmol) of N-methylmorpholine and 2.4 ml (18.33 mmol) of isobutyl chloroformate are added dropwise at −15° C. to a solution of 5.0 g (18.33 mmol) of 1-chloro-dibenz|b.f|oxepine-10-carboxylic acid in dimethoxyethane. After 5 minutes filtration is carried out and at −15° C. a solution of 1.39 g (36.67 mmol) of sodium borohydride in 15 ml of water is added dropwise to the filtrate. The mixture is stirred for 15 minutes at −15 °C., then 35 ml of 1N hydrochloric acid are added and the mixture is allowed to warm to room temperature. The reaction mixture is rendered basic with sodium hydroxide and extracted 4× with ethyl acetate. The organic phase is washed 1× with water, dried over sodium sulfate and concentrated. 4.58 g (17.7 mmol) =96.6% of crude (1-chloro-dibenz|b,f|oxepin-10-yl)-methanol are obtained in the form of a yellow oil; TLC (silica gel; ethyl acetate/hexane=1:1; UV): $R_f$=0.46; $^1$H-NMR (CDCl$_3$, 200 MHz): 2.42 (sbr, 1H); 4.71 (s, 2H); 7.10–7.45 (m, 7H).

g) 10-Bromomethyl-1-chloro-dibenz|b,f|oxepine 4.58 g (17.70 mmol) of (1-chloro-dibenz|b,f|oxepin-10-yl)-methanol are heated under reflux in 50 ml of 48% hydrobromic acid for 2 hours. The mixture is cooled, water is added and the mixture is extracted 3× with ethyl acetate. The organic phases are washed with brine, dried over sodium sulfate and concentrated. 5.57 g of crude product are obtained which becomes solid on being left to stand (3 days). Recrystallisation from tert-butyl methyl ether/hexane yields 2.205 g (6.86 mmol)=38.7% of 10-bromomethyl-1-chloro-dibenz|b,f|oxepine in the form of light-beige crystals; TLC (silica gel; ethyl acetate; UV): $R_f$=0.73; $^1$H-NMR (CDCl$_3$, 200 MHz): 4.60 (s, 2H); 7.15–7.58 (m, 8H).

EXAMPLE 13

1-(1-Chloro-dibenz|b,f|oxepin-10-ylmethyl)-pyrrolidine hydrochloride

Preparation analogous to Example 2 from 10-bromomethyl-1-chloro-dibenz[b,f]oxepine with pyrrolidine. Yield: 51%, yellow foam; melting point: not determined, (yellow foam); $^1$H-NMR (CDCl$_3$, 200 MHz): 1.78 (m, 4H); 2.65 (m, 4H); 3.65 (s, 2H); 7.10–7.45 (m, 7H) 7.68 (d, 1H).

EXAMPLE 14

N-(1-Chloro-dibenz|b,f|oxepin-10-ylmethyl)-N-methyl-N-propylamine hydrochloride

Preparation analogous to Example 2 from 10-bromomethyl-1-chloro-dibenz[b,f]oxepine with N-methyl-propylamine; yield: 25%; beige solid; melting point: not determined, (beige foam); $^1$H-NMR (CDCl$_3$, 200 MHz): 0.88 (t, 3H); 1.55 (m, 2H); 2.28 (s, 3H); 2.43 (t, 2H); 3.55 (s, 2H); 7.08–7.35 (m, 7H); 7.61 (d, 1H).

EXAMPLE 15

N-Methyl-N-prop-2-ynyl-N-(3-trifluoromethyl-dibenz|b,f|oxepin-10-ylmethyl)amine

Preparation analogous to Example 2 from 10-bromomethyl-3-trifluoromethyl-dibenz|b,f|oxepine and N-methyl-propargylamine. As free base chromatographed on silica gel with hexane/ethyl acetate=1:1 and crystallised from a small amount of petroleum ether; yield: 56%; melting point: 66°–68° C.; $^1$H-NMR (CDCl$_3$, 200 MHz): 1.80 (t, 1H); 2.41 (s, 3H); 3.46 (d, 2H); 3.65 (sbr, 1H); 7.15–7.58 (m, 7H); MS: 343 (M$^+$), 342, 300, 276, 249, 205, 178, 152.

The starting material can be prepared, for example, in the following manner:

a) 2-Phenoxy-4-trifluoromethyl-benzaldehyde

Preparation analogous to Example 12 from 2-fluoro-4-trifluoromethyl-benzaldehyde and phenol. Yield: 78%, light-coloured crystals, crystallised from hexane; melting point: 57°–59° C.; TLC (silica gel; ethyl acetate/hexane=1:1; UV): $R_f$=0.71; $^1$H-NMR (CDCl$_3$, 200 MHz): 7.08–7.50 (m, 7H); 8.05 (d, 1H); 10.60 (s, 1H). MS: 266/265 (M$^+$), 217, 188.

b) 3-Trifluoromethyl-dibenz|b,f|oxepine-10-carboxylic acid

A mixture of 10.0 g (37.59 mmol) of 2-phenoxy-4-trifluoromethyl-benzaldehyde, 10.09 g (56.40 mmol) of hippuric acid and 3.70 g (45.10 mmol) of sodium acetate in 38 ml of acetic anhydride is heated at 85° C. for 80 minutes, then cooled to 32° C., 19 ml of water are added and the mixture is heated at 65° C. for 30 minutes. After cooling the mixture to approximately 5° C., 19 ml of concentrated sulfuric acid are added dropwise and the mixture is then heated under reflux (bath: 140° C.) for 2 hours. The brown precipitate that forms on cooling is filtered and washed with 50% acetic acid, washed with water until neutral and dried to yield 7.42 g (24.23 mmol)=65% of 3-trifluoromethyl-dibenz|b,f|oxepine-10-carboxylic acid in the form of beige crystals; melting point: 180° C.; $^1$H-NMR (CDCl$_3$, 200 MHz): 7.2–7.65 (m, 8H); 8.09 (s, 1H).

c) (3-Trifluoromethyl-dibenz|b,f|oxepin-10-yl)-methanol

Preparation analogous to Example 12f) from 3-trifluoromethyl-dibenz|b,f|oxepine-10-carboxylic acid. Product crystallised from tert-butyl methyl ether/hexane; yield: 75.2%; white crystals; TLC (silica gel; ethyl acetate/hexane=1:1; UV): $R_f$=0.31; $^1$H-NMR (CDCl$_3$, 200 MHz): 2.76 (sbr, 1H); 4.72 (s, 2H); 6.96 (s, 1H); 7.16–7.48 (m, 7H).

d) 10-Bromomethyl-3-trifluoromethyl-dibenz|b,f|oxepine

Preparation analogous to Example 12g) from (3-trifluoromethyl-dibenz|b,f|oxepin-10-yl)-methanol. Product crystallised from hexane; yield: 92%, white crystals; TLC (silica gel; ethyl acetate/hexane=1:1; UV): $R_f$=0.70; $^1$H-NMR (CDCl$_3$, 200 MHz): 4.55 (s, 2H); 7.04 (s, 1H); 7.20–7.60 (m, 7H); MS: 356/354 (M$^+$), 275, 249, 219, 206, 205, 178, 176.

EXAMPLE 16

1-(3-Trifluoromethyl-dibenz|b,f|oxepin-10-ylmethyl)-pyrrolidine hydrochloride

Preparation analogous to Example 2 from 10-bromomethyl-3-trifluoromethyl-dibenz|b,f|oxepine and pyrrolidine. Yield: 86%; light-beige crystals; melting point: >220° C.; $^1$H-NMR (CD$_3$OD, 200 MHz): 1.90–2.20 (m, 4H); 2.25 (m, 2H); 3.55 (m, 2H); 4.59 (s, 2H); 7.30–7.70 (m, 8H). MS: 345 (M$^+$, free base), 276, 249, 205, 178, 152.

EXAMPLE 17

N-(7-Chloro-dibenz|b,f|oxepin-10-ylmethyl)-N-methyl-N-prop-2-ynylamine hydrochloride Preparation analogous to Example 2 from 10-bromomethyl-7-chloro-dibenz|b,f|oxepine and N-methyl-propargylamine. Yield: 68%; beige crystals; melting point: 189°–195° C.; $^1$H-NMR (CD$_3$OD, 200 MHz): 2.96 (s, 3H); 3.49 (m(t), 1H); 4.15 (m(d), 2H); 4.60 (sbr, 1H); 7.20–7.65 (m, 8H) ; MS: 309 (M$^+$, free base), 266, 244, 242, 241, 215, 205, 176, 163, 152.

The starting material can be prepared, for example, in the following manner:

a) 2-(3-Chlorophenoxy)benzaldehyde

Preparation analogous to Example 12a) from 2-fluorobenzaldehyde and 3-chlorophenol. Yield: 69%; yellow oil after bulb tube distillation (150°–180° C., 0.001 torr); $^1$H-NMR (CDCl$_3$, 200 MHz): 6.92–7.38 (m, 6H); 7.95 (m, 1H); 10.48 (s, 1H).

b) 7-Chloro-dibenz|b,f|oxepine-10-carboxylic acid

Preparation analogous to Example 15b) from 2-(3-chlorophenoxy)-benzaldehyde. Crystallised from tert-butyl methyl ether/hexane. Yield: 25%; light-yellow crystals; TLC (silica gel; ethyl acetate/hexane=1:1; UV): $R_f$=0.15; $^1$H-NMR (CDCl$_3$, 200 MHz): 7.05–7.50 (m, 8H); 7.90 (s, 1H). MS: 274/272 (M$^+$).

c) (7-Chloro-dibenz|b.f|oxepin-10-yl)methanol

Preparation analogous to Example 12 f) aus 7-chloro-dibenz|b.f|oxepine-10-carboxylic acid. Yield: 94% in the form of an oil; TLC (silica gel; ethyl acetate/hexane=1:1; UV): $R_f$=0.38; $^1$H-NMR (CDCl$_3$, 200 MHz): 1.72 (sbr, 1H); 4.67 (s, 2H); 6.91 (s, 1H); 7.10–7.40 (m, 7H) ; MS: 260/258 (M$^+$), 217/215.

d) 10-Bromomethyl-7-chloro-dibenz|b.f|oxepine

Preparation analogous to Example 12g) from (7-chloro-dibenz|b.f|oxepin-10-yl)-methanol. Product crystallised from hexane. Yield: 56%; almost white crystals; melting point: 117°–119° C.; TLC (silica gel; ethyl acetate/hexane= 1:1; UV): $R_f$=0.70; $^1$H-NMR (CDCl$_3$, 200 MHz): 4.51 (s, 2H); 7.03 (s, 1H); 7.24–7.50 (m, 7H) ; MS: 324/322/320 (M$^+$, Br—Cl-isotope distribution), 243/241 (Cl-isotope distribution), 206/205, 178/176.

EXAMPLE 18

1-(7-Chloro-dibenz|b.f|oxepin-10-ylmethyl)-pyrrolidine hydrochloride

Preparation analogous to Example 2 from 10-bromomethyl-7-chloro-dibenz|b.f|oxepine and pyrrolidine. Yield: 45%; melting point: >225° C. decomposition. $^1$H-NMR (CD$_3$OD, 200 MHz): 1.95–2.20 (m, 4H); 3.25 (m 2H); 3.55 (m, 2H); 4.52 (s, 2H); 7.20–7.45 (m, 7H); 7.60 (d, 1H).

MS: 311 (M$^+$, free base), 244, 242, 241,215, 205,178, 176, 163, 152.

EXAMPLE 19

N-(8-Methoxy-dibenz|b.f|oxepin-10-ylmethyl)-N-methyl-N-prop-2-ynylamine hydrochloride Preparation analogous to Example 2 from 10-bromomethyl-8-methoxy-dibenz|b.f|oxepine and N-methyl-propargylamine. Yield: 35%, white crystals; melting point: decomposition >60° C. $^1$H-NMR (CDCl$_3$, 200 MHz): 2.33 (t, 1H); 2.42 (s, 3H); 3.48 (d, 2H); 3.62 (s, 2H); 3.78 (s, 3H); 6.80–6.90 (m, 2H); 7.05–7.32 (m, 6H).

The starting material can be prepared, for example, in the following manner:

a) 8-Methoxy-dibenz|b.f|oxepine-10-carboxylic acid

Preparation analogous to Example 15 b) from 2-(4-methoxy-phenoxy)-benzaldehyde. Silica gel chromatography (eluant: ethyl acetate/hexane=1:1), then crystallisation from ethyl acetate/hexane=7:3. Yield: 19%, beige crystals; melting point: 150° C.; TLC (silica gel; ethyl acetate/ hexane=1:1; UV): $R_f$=0.58; $^1$H-NMR (CDCl$_3$, 200 MHz): 3.80 (s, 3H); 6.92 (dd, 1H); 7.17–7.45 (m, 7H); 8.13 (s, 1H); MS: 268 (M$^+$).

b) (8-Methoxy-dibenz|b.f|oxepin-10-yl)methanol

Preparation analogous to Example 12f) from 8-methoxy-dibenz|b.f|oxepine-10-carboxylic acid. Yield: 96% in the form of a brown oil; TLC (silica gel; ethyl acetate/hexane= 1:1; UV): $R_f$=0.31; $^1$H-NMR (CDCl$_3$, 300 MHz): 1.80 (sbr, 1H); 3.78 (s, 3H); 4.69 (s, 2H); 6.82–7.33 (m, 8H) MS: 254 (M$^+$), 211, 182, 181, 168, 165, 153, 152.

c) 10-Bromomethyl-8-methoxy-dibenz|b.f|oxepine

Preparation analogous to Example 12g) from (8-methoxy-dibenz|b.f|oxepin-10-yl)-methanol. Product crystallised from hexane/tert-butyl methyl ether. Yield: 96%, light-brown crystals; TLC (silica gel; ethyl acetate; UV): $R_f$=0.70; $^1$H-NMR (CDCl$_3$, 200 MHz): 3.80 (s, 3H); 4.52 (s, 2H); 6.86–7.37 (m, 8H).

EXAMPLE 20

N-(8-Tert-butyl-dibenz|b.f|oxepin-10-ylmethyl)-N-methyl-N-prop-2-ynylamine hydrochloride Preparation analogous to Example 2 from 10-bromomethyl-tert-butyl-dibenz|b.f|oxepine and N-methyl-propargylamine. Yield: 24%, beige crystals; melting point: 135°–145° C.; $^1$H-NMR (CD$_3$OD, 200 MHz): 1.35 (s, 9H); 2.96 (s, 3H); 3.52 (t, 1H); 4.17 (d, 2H); 7.15–7.60 (m, 9H); EI-MS: 331(M$^+$), 264, 249, 237, 207.

The starting material can be prepared, for example, in the following manner:

a) 2-(4-Tert-butyl-phenoxy)benzaldehyde

Preparation analogous to Example 12a) from 2-fluoro-benzaldehyde and 4-tert-butylphenol. Yield: 77%, yellow oil after high vacuum distillation (93°–100° C., 0.9 mbar); TLC (silica gel; hexane/ethyl acetate=1:1; UV): $R_f$=0.65; $^1$H-NMR (CDCl$_3$, 200 MHz): 1.35 (s, 9H); 6.75–7.55 (m, 7H); 7.92 (dd, 1H) MS: 254 (M$^+$), 239.

b) 8-Tert-butyl-dibenz|b.f|oxepine-10-carboxylic acid

Preparation analogous to Example 15b) from 2-(4-tert-butyl-phenoxy)-benzaldehyde. Crystallised from hexane. Yield: 16%, light-yellow crystals; melting point: 72° C.; TLC (silica gel; hexane/ethyl acetate=4:1; UV): $R_f$=0.46; $^1$H-NMR (CDCl$_3$, 200 MHz): 1.31 (s, 9H); 7.15–7.45 (m, 8H); 7.62 (d, 1H); 8.10 (s, 1H); MS: 295 (M$^+$), 279, 239.

c) (8-Tert-butyl-dibenz|b.f|oxepin-10-yl)methanol

Preparation analogous to Example 12f) from 8-methoxy-dibenz|b.f|oxepine-10-carboxylic acid. Yield: 30% in the form of an oil after chromatography (silica gel; hexane/ethyl acetate=9:1) and bulb tube distillation (100° C., 0.3 mbar) ; TLC (silica gel; hexane/ethyl acetate=9:1; UV): $R_f$=0.11. 1H-NMR (CDCl$_3$, 200 MHz): 1.30 (s, 9H); 1.72 (sbr, 1H); 4.75 (s, 2H); 6.92 (s, 1H); 7.06–7.45 (m, 7H); MS: 280 (M$^+$), 265, 237.

d) 10- Bromomethyl-8-tert-butyl-dibenz|b.f|oxepine

Preparation analogous to Example 12g) from (8-tert-butyl-dibenz|b.f|oxepin-10-yl)-methanol. Yield: 85%, brown oil; TLC (silica gel; ethyl acetate/hexane=1:1; UV): $R_f$=0.58; $^1$H-NMR (CDCl$_3$, 200 MHz): 1.31 (s, 9H); 4.58 (s, 2H); 7.05–7.45 (m, 7H); 7.60 (d, 1H); MS: 344/342 (M$^+$), 263.

EXAMPLE 21

1-(8-Tert-butyl-dibenz|b.f|oxepin-10-ylmethyl)-pyrrolidine hydrochloride

Preparation analogous to Example 2 from 10-bromomethyl-8-tert-butyl-dibenz|b.f|oxepine (see above) and pyrrolidine. Yield: 76%, yellow crystals; melting point: 184°–185° C.; $^1$H-NMR (CD$_3$OD, 200 MHz): 1.48 (s, 9H); 1.95–2.22 (mbr, 4H); 3.25 (mbr, 2H); 3.53 (mbr, 2H); 4.57 (s, 2H); 7.18–7.58 (m, 8H) ; MS: 333 (M$^+$, free base), 264, 249, 237, 207.

EXAMPLE 22

N-(6-Chloro-dibenz|b.f|oxepin-10-ylmethyl)-N-methyl-N-prop-2-ynylamine hydrochloride Preparation analogous to Example 2 from 10-bromomethyl-6-bromo-dibenz|b.f|oxepine and N-methyl-propargylamine. Yield: 14%, white crystals; melting point: 188°–190° C.; $^1$H-NMR (free base) (CDCl$_3$, 200 MHz): 2.28 (t, 1H); 2.40 (s, 3H); 3.45 (d, 2H); 3.63 (s, 2H); 6.93–7.50 (m, 8H) ; MS: 310, 312 (M$^+$+1, free base).

The starting material can be prepared, for example, in the following manner:

a) [2-(2-Chlorophenoxy)phenyl]methanol

Preparation analogous to Example 12b) from 2-(2-chlorophenoxy)-benzoic acid distilled under a high vacuum. Yield: 53%, yellow oil; TLC (silica gel; ethyl acetate): $R_f=0.74$; $^1$H-NMR (CDCl$_3$, 200 MHz): 2.60 (sbr, 1H); 4.78 (s, 2H); 6.70–7.50 (m, 8H). FD-MS: 234, 236 (M$^+$).

b) [2-(2-Chlorophenoxy)-phenyl]-bromomethane

Preparation analogous to Example 12c) from [2-(2-chlorophenoxy)-phenyl]-methanol. Crystallised from hexane. Yield: 97% crude, slightly brownish oil; $^1$H-NMR (CDCl$_3$, 200 MHz): 4.68 (s, 2H); 6.70 (dd, 1H); 7.02–7.52 (m, 7H) ; TLC (silica gel; hexane/ethyl acetate=7:3; UV): $R_f=0.69$.

c) [2-(2-Chlorophenoxy)-phenyl]acetonitrile

Preparation analogous to Example 12d) from [2-(2-chlorophenoxy)-phenyl]-bromomethane. Yield: 99%, crude, brown oil; TLC (silica gel; hexane/ethyl acetate=7:3; UV): $R_f=0.52$; $^1$H-NMR (CDCl$_3$, 200 MHz): 3.90 (s, 2H); 6.65–7.53 (m, 8H) ; MS: 295 (M$^+$), 279, 239.

d) 6-Bromo-dibenz[b,f]oxepine-10-carboxylic acid

Preparation analogous to Example 12e) from [2-(2-chlorophenoxy)phenyl]acetonitrile. Yield: 85%, yellow crystals; $^1$H-NMR (CDCl$_3$, 200 MHz): 6.70–7.50 (m, 7H); 8.32 (dd, 1H).

e) (6-Bromo-dibenz[b,f]oxepin-10-yl)methanol

Preparation analogous to Example 12f) from 6-bromo-dibenz[b,f]oxepine-10-carboxylic acid. Yield: 99% crude, brown oil; TLC (silica gel; hexane/ethyl acetate=7:3; UV): $R_f=0.07$; $^1$H-NMR (CDCl$_3$, 200 MHz): 3.54 (s, 2H); 6.70–7.49 (m, 8H).

f) 10-Bromomethyl-6-bromo-dibenz[b,f]oxepine

Preparation analogous to Example 12 g) from (6-bromo-dibenz[b,f]oxepin-10-yl)-methanol. Yield: 8%, brownish-orange oil; $^1$H-NMR (CDCl$_3$, 200 MHz): 4.53 (s, 2H); 7.05–7.60 (m, 8H).

EXAMPLE 23

1-(6-Chloro-dibenz[b,f]oxepin-10-ylmethyl) pyrrolidine hydrochloride

Preparation analogous to Example 2 from 10-bromomethyl-6-bromo-dibenz[b,f]oxepine and pyrrolidine. Yield: 20%, beige crystals; melting point: 198°–200° C.; $^1$H-NMR (free base) (CDCl$_3$, 200 MHz): 1.78 (m, 4H); 2.57 (m, 4H); 3.62 (s, 2H); 6.89–7.50 (m, 8H) ; MS: 312, 314 (M$^+$+1, free base).

EXAMPLE 24

In a manner analogous to that described in Examples 1 to 23 it is also possible to prepare the following:

N-(1-fluoro-dibenz[b,f]oxepin-10-ylmethyl)-N-methyl-N-prop-2-ynylamine;

1-(1-fluoro-dibenz[b,f]oxepin-10-ylmethyl)pyrrolidine;

N-benzyl-N-(dibenz[b,f]oxepin-10-ylmethyl)amine alias 10-benzylaminomethyl-dibenz[b,f]oxepine;

N-benzyl-N-(dibenz[b,f]oxepin-10-ylmethyl)-N-methylamine;

N-(dibenz[b,f]oxepin-10-ylmethyl)-N-propyl-N-benzylamine and

N-allyl-N-benzyl-N-(dibenz[b,f]oxepin-10-ylmethyl)amine and salts thereof.

EXAMPLE 25

Tablets each comprising 50 mg of 1-(dibenz[b,f]oxepin-10-ylmethyl)pyrrolidine or a salt, for example the hydrochloride, thereof, may be prepared as follows:

| Composition (10 000 tablets) | |
|---|---|
| active ingredient | 500.0 g |
| lactose | 500.0 g |
| potato starch | |
| gelatin | 8.0 g |
| talc | 60.0 g |
| magnesium stearate | 10.0 g |
| silicon dioxide (highly dispersed) | 20.0 g |
| ethanol | q.s. |

The active ingredient is mixed with the lactose and 292 g of the potato starch, and the mixture is moistened with an ethanolic solution of the gelatin and granulated through a sieve. After drying, the remainder of the potato starch, the magnesium stearate, the talc and the silicon dioxide are mixed in and the mixture is compressed to form tablets each weighing 145.0 mg and comprising 50.0 mg of active ingredient; if desired, the tablets may be provided with dividing notches for finer adaptation of the dose.

EXAMPLE 26

A sterile-filtered aqueous gelatin solution containing 20% cyclodextrins as solubiliser, comprising as active ingredient 3 mg of 1-(dibenz[b,f]oxepin-10-ylmethyl)-pyrrolidine or of a salt, for example the hydrochloride, thereof, is so mixed, with heating, under aseptic conditions with a sterile gelatin solution comprising phenol as preservative that 1.0 ml of solution has the following composition:

| active ingredient | 3 mg |
|---|---|
| gelatin | 150.0 mg |
| phenol | 4.7 mg |
| dist. water with 20% cyclodextrins as solubiliser | 1.0 ml |

EXAMPLE 27

For the preparation of a sterile dry substance for injection, comprising 5 mg of 1-(dibenz[b,f]oxepin-10-ylmethyl) pyrrolidine or of a salt, for example the hydrochloride, thereof, 5 mg of one of the compounds of formula I mentioned in the preceding Examples are dissolved as active ingredient in 1 ml of an aqueous solution containing 20 mg of mannitol and 20% cyclodextrins as solubiliser. The solution is sterile-filtered and, under aseptic conditions, filled into a 2 ml ampoule, deep-frozen and lyophilised. Before use, the lyophilisate is dissolved in 1 ml of distilled water or 1 ml of physiological saline. The solution is administered intramuscularly or intravenously. The formulation can also be filled into double-chamber disposable syringes.

EXAMPLE 28

10,000 film-coated tablets, each containing 100 mg of 1-(dibenz[b,f]oxepin-10-ylmethyl)pyrrolidine or a salt, for example the hydrochloride, thereof, may be prepared as follows:

| active ingredient | 1000 g |
| --- | --- |
| corn starch | 680 g |
| colloidal silicic acid | 200 g |
| magnesium stearate | 20 g |
| stearic acid | 50 g |
| sodium carboxymethyl starch | 250 g |
| water | q.s. |

A mixture of one of the compounds of formula I mentioned in the preceding Examples as active ingredient, 50 g of corn starch and the colloidal silicic acid is processed with a starch paste made from 250 g of corn starch and 2.2 kg of demineralised water to form a moist mass. The mass is forced through a sieve of 3 mm mesh size and dried at 45° for 30 minutes in a fluidised bed drier. The dried granules are pressed through a sieve of 1 mm mesh size, mixed with a previously sieved mixture (1 mm sieve) of 330 g of corn starch, the magnesium stearate, the stearic acid and the sodium carboxymethyl starch and compressed to form slightly convex tablets.

EXAMPLE 29

In a manner analogous to that described in Examples 25 to 28, it is also possible to prepare pharmaceutical compositions comprising a different compound according to any one of Examples 1 to 24 or
1-(dibenz[b.f]oxepin-10-ylmethyl)-4-methyl-piperazine;
1-(dibenz[b.f]oxepin-10-ylmethyl)-4-(2-hydroxyethyl)-piperazine;
10-allylaminomethyldibenz[b.f]oxepine;
10-aminomethyldibenz[b.f]oxepine;
10-benzylaminomethyldibenz[b.f]oxepine;
10-butylaminomethyldibenz[b.f]oxepine;
N,N-diethyl-N-(dibenz[b.f]oxepin-10-ylmethyl)amine;
N-(dibenz[b.f]oxepin-10-ylmethyl)-N,N-dimethylamine;
N-(dibenz[b.f]oxepin-10-ylmethyl)-N-methylamine;
1-(dibenz[b.f]oxepin-10-ylmethyl)pyrrolidine;
N-[1-(dibenz[b.f]oxepin-10-ylethyl)-N,N-dimethylamine;
N-[1-(dibenz[b.f]oxepin-10-ylethyl)-N-methylamine;
1-(8-methoxy-dibenz[b.f]oxepin-10-ylmethyl)-4-methyl-piperazine;
(8-methoxy-dibenz[b.f]oxepin-10-ylmethyl)-dimethylamine;
(8-methoxy-dibenz[b.f]oxepin-10-ylmethyl)-methylamine;
(8-chloro-dibenz[b.f]oxepin-10-ylmethyl)-dimethylamine;
(8-chloro-dibenz[b.f]oxepin-10-ylmethyl)-diethylamine
or in each case a salt thereof.

What is claimed is:

1. A method of treating neurodegenerative disease, which comprises administering an anti-neurodegeneratively effective amount of a compound of formula I

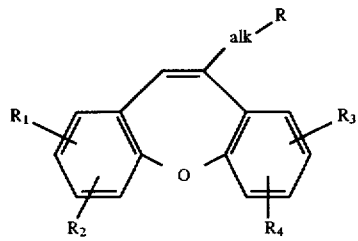

wherein alk is a divalent aliphatic radical,

R is an amino group that is mono- or di-substituted by monovalent aliphatic at least one monovalent radical being a substituted or unsubstituted lower alkynyl group, and $R_1$, $R_2$, $R_3$ and $R_4$ are each, independently of the others, hydrogen, lower alkyl, lower alkoxy, halogen or trifluoromethyl, or a pharmaceutically acceptable salt thereof to a warm-blooded organism in need of such treatment.

2. A method according to claim 1 wherein a compound of the formula I in which
1-N-(Dibenz[b.f]oxepin-10-ylmethyl)-N-prop-2-ynylamine,
N-ally-N-(dibenz[b.f]oxepin-10-ylmethyl)amine,
N-benzyl-N-(dibenz[b.f]oxepin-10-ylmethyl)amine,
N-(dibenz[b.f]oxepin-10-ylmethyl)-N-prop-2-ynylamine,
N-(dibenz[b.f]oxepin-10-ylmethyl)-N-propylamine,
N-allyl-N-(dibenz[b.f]oxepin-10-ylmethyl)-N-methylamine,
N-(dibenz[b.f]oxepin-10-ylmethyl)amine,
N-(dibenz[b.f]oxepin-10-ylmethyl)-N-methyl-N-propylamine,
1-dibenz[b.f]oxepin-10-ylmethyl-piperidine,
4-dibenz[b.f]oxepin-10-ylmethyl-morpholine,
N-(-1-chloro-dibenz[b.f]oxepin-10-ylmethyl)-N-methyl-N-prop-2-ynylamine,
N-(dibenz[b.f]oxepin-10-ylmethyl)-N-prop-2-ynylamine,
1-(1-chloro-dibenz[b.f]oxepin-10-ylmethyl)-pyrrolidine,
N-(1-chloro-dibenz[b.f]oxepin-10-ylmethyl)-N-methyl-N-propylamine,
N-methyl-N-prop-2-ynyl-N-(3-trifluoromethyl-dibenz[b.f]oxepin-10-ylmethyl)amine,
1-(3-trifluoromethyl-dibenz[b.f]oxepin-10-ylmethyl)-pyrrolidine,
N-(7-chloro-dibenz[b.f]oxepin-10-ylmethyl)-N-methyl-N-prop-2-ynylamine,
1-(7-chloro-dibenz[b.f]oxepin-10-ylmethyl)pyrrolidine,
N-(8-methoxy-dibenz[b.f]oxepin-10-ylmethyl)-N-methyl-N-prop-2-ynylamine,
N-(8-tert-butyl-dibenz[b.f]oxepin-10-ylmethyl)-N-methyl-N-prop-2-ynylamine,
N-(6-chloro-dibenz[b.f]oxepin-10-ylmethyl)-N-methyl-N-prop-2-ynylamine,
1-(6-chloro-dibenz[b.f]oxepin-10-ylmethyl)pyrrolidine,
N-(1-fluoro-dibenz[b.f]oxepin-10-ylmethyl)-N-methyl-N-prop-2-ynylamine,
1-(1-fluoro-dibenz[b.f]oxepin-10-ylmethyl)pyrrolidine,
N-benzyl-N-(dibenz[b.f]oxepin-10-ylmethyl)-N-methylamine,
N-(dibenz[b.f]oxepin-10-ylmethyl)-N-propyl-N-benzylamine,
N-allyl-N-benzyl-N-(dibenz[b.f]oxepin-10-ylmethyl)amine or
N-(7-chloro-dibenz[b.f]oxepin-10-ylmethyl)-N-methyl-N-prop-2-ynylamine or a salt of any one thereof is utilized.

* * * * *